United States Patent
Gilbert et al.

(10) Patent No.: US 8,278,069 B2
(45) Date of Patent: Oct. 2, 2012

(54) **IDENTIFICATION OF A β-1,3-N-ACETYLGALACTOSAMINYLTRANSFERASE (CGTE) FROM *CAMPYLOBACTER JEJUNI* LIO87**

(75) Inventors: Michel Gilbert, Gatineau (CA); Warren Wakarchuk, Ottawa (CA); Scott Houliston, Ottawa (CA)

(73) Assignee: National Research Council of Canada, Ottawa, Ontario (CA)

( * ) Notice: Subject to any disclaimer, the term of this patent is extended or adjusted under 35 U.S.C. 154(b) by 0 days.

(21) Appl. No.: 11/911,318

(22) PCT Filed: Apr. 7, 2006

(86) PCT No.: PCT/CA2006/000544
§ 371 (c)(1),
(2), (4) Date: May 28, 2008

(87) PCT Pub. No.: WO2006/108273
PCT Pub. Date: Oct. 19, 2006

(65) Prior Publication Data
US 2009/0215116 A1 Aug. 27, 2009

Related U.S. Application Data

(60) Provisional application No. 60/670,608, filed on Apr. 11, 2005.

(51) Int. Cl.
*C12P 19/00* (2006.01)
*C12P 19/18* (2006.01)
*C12N 9/10* (2006.01)

(52) U.S. Cl. .............................. 435/72; 435/97; 435/193
(58) Field of Classification Search ........................ None
See application file for complete search history.

(56) References Cited

OTHER PUBLICATIONS

Database: Uniport, Gilbert et al. Accession No. Q8KWR0 (2002).*
J.A. Campbell, G.J. Davies, V. Bulone and B. Henrissat, A classification of nucleotide-diphospho-sugar glycosyltransferases based on amino acid sequence similarities, Biochem. J. (1997) 326:929-938.
NCBI Accession No. AF400669 Aug. 2, 2002. Gilbert, M., et al. Sequencing of the lipo-oligosaccharide biosynthesis locus of *Campylobacter jejuni* LIO87.
Gilbert, M., et al., "Biosynthesis of ganglioside mimics in *Campylobacter jejuni* OH4384. Identification of the glycosyltransferase genes, enzymatic synthesis of model compounds, and characterization of nanomole amounts by 600-mhz $^1$H and $^{13}$C NMR analysis," 2000, *J. Biol. Chem.*, vol. 275, pp. 3896-3906.
Gilbert, M., et al., "The genetic bases for the variation in the lipo-oligosaccharide of the mucosal pathogen, *Campylobacter jejuni*. Biosynthesis of sialylated ganglioside mimics in the core oligosaccharide," 2002, *J. Biol. Chem.*, vol. 277, pp. 327-337.
Parker, C.T., et al., "Comparison of *Campylobacter jejuni* lipooligosaccharide biosynthesis loci from a variety of sources," 2005, *J. Clin. Microbiol.*, vol. 43, pp. 2771-2781.

* cited by examiner

*Primary Examiner* — Nashaat Nashed
(74) *Attorney, Agent, or Firm* — Nada Jain, PC

(57) ABSTRACT

The invention relates to β-1,3-N-acetylgalactosaminyltransferase polypeptides, nucleic acids that encode the polypeptides, and methods of using the polypeptides.

15 Claims, 3 Drawing Sheets

FIG. 3

```
CD-Length = 168 residues,   95.8% aligned
            Score = 108 bits (260), Expect = 1e-24

Query:   5  SIILPTFNVEKYIAKALESCINQSFKDIEIIVVDDCGSDKSIDIAKEYAKKDERIKIIHN   64
Sbjct:   1  SVIIPTYNEEKYLEETLESLLAQTYPNFEIIVVDDGSTDGTVEIAEEYAKNDPRIRVIRL   60

Query:  65  EENLGLLRARYEGVKAAGGGYIMFLDPDDYLELNACEECVRIINTEKESDFIWFDFIYKR  124
Sbjct:  61  EENLGKAAARNAGLKHATGDYILFLDADDEVAPDWLEKIVELL--EKNGADIVIGSRVAI  118

Query: 125  ISGVINRGNFLQDQTFTIFEYCENIIQNKNICYWNLCSKLIK  167
Sbjct: 119  FGETRLDGRALRMELLLLGKLGARSLGLKVLFLIGSNALYRR  161
```

IDENTIFICATION OF A β-1,3-N-ACETYLGALACTOSAMINYLTRANSFERASE (CGTE) FROM *CAMPYLOBACTER JEJUNI* LIO87

CROSS-REFERENCES TO RELATED APPLICATIONS

This application is a U.S. National Stage of International Patent Application No.
PCT/CA2006/000544, filed Apr. 7, 2006, and claims the benefit of U.S. Provisional Application No. 60/670,608, filed Apr. 11, 2005, which are herein incorporated by reference in their entirety for all purposes.

BACKGROUND OF THE INVENTION

Carbohydrates are now recognized as being of major importance in many cell-cell recognition events, notably the adhesion of bacteria and viruses to mammalian cells in pathogenesis and leukocyte-endothelial cell interaction through selectins in inflammation (Varki (1993) *Glycobiology* 3: 97-130). Moreover, sialylated glycoconjugates that are found in bacteria (Preston et al. (1996) *Crit. Rev. Microbiol.* 22:139-180; Reuter et al. (1996) *Biol. Chem. Hoppe-Seyler* 377:325-342) are thought to mimic oligosaccharides found in mammalian glycolipids to evade the host immune response (Moran et al. (1996) *FEMS Immunol. Med. Microbiol.* 16:105-115). Molecular mimicry of host structures by the saccharide portion of lipopolysaccharide (LPS) is considered to be a virulence factor of various mucosal pathogens, which use this strategy to evade a host immune response (Moran et al. (1996) *FEMS Immunol. Med. Microbiol.* 16: 105-115; Moran et al. (1996) *J. Endotoxin Res.* 3: 521-531).

The oligosaccharide structures involved in these and other processes are potential therapeutic agents, but they are time consuming and expensive to make by traditional chemical means. A very promising route to production of specific oligosaccharide structures is through the use of the enzymes which make them in vivo, the glycosyltransferases. Such enzymes can be used as regio- and stereoselective catalysts for the in vitro synthesis of oligosaccharides (Ichikawa et al. (1992) *Anal. Biochem.* 202: 215-238).

Large scale enzymatic synthesis of oligosaccharides depends on the availability of sufficient quantities of the required glycosyltransferases. However, production of glycosyltransferases in sufficient quantities for use in preparing oligosaccharide structures has been problematic. Expression of many mammalian glycosyltransferases has been achieved involving expression in eukaryotic hosts which can involve expensive tissue culture media and only moderate yields of protein (Kleene et al. (1994) *Biochem. Biophys. Res. Commun.* 201: 160-167; Williams et al. (1995) *Glycoconjugate J.* 12: 755-761). Expression in *E. coli* has been achieved for mammalian glycosyltransferases, but these attempts have produced mainly insoluble forms of the enzyme from which it has been difficult to recover active enzyme in large amounts (Aoki et al. (1990) *EMBO. J.* 9:3171-3178; Nishiu et al. (1995) *Biosci. Biotech. Biochem.* 59 (9): 1750-1752). Furthermore, because of the biological activity of their products, mammalian sialyltransferases generally act in specific tissues, cell compartments and/or developmental stages to create precise glycan structures. Identification of glycosyltransferases that can be used in enzymatic synthesis of commercially valuable oligosaccharides and that can be produced in large quantities would thus be useful in the development of these technologies. The present invention fulfills this and other needs.

BRIEF SUMMARY OF THE INVENTION

In one aspect the present invention provides an isolated or recombinant β-1,3-N-acetylgalactosaminyltransferase polypeptide, that includes an amino acid sequence with at least 80% identity to SEQ ID NO:2. The β-1,3-N-acetylgalactosaminyltransferase polypeptide transfers a galactose moiety from a donor substrate to an acceptor substrate. A galactose moiety can be either, e.g., galactose or GalNAc. In a preferred embodiment, the galactose moiety is GalNAc. In another embodiment, the β-1,3-N-acetylgalactosaminyltransferase polypeptide includes an amino acid sequence with at least 90% or 95% identity to SEQ ID NO:2. In another embodiment, the β-1,3-N-acetylgalactosaminyltransferase polypeptide comprises the amino acid sequence of SEQ ID NO:2.

In another aspect, the present invention provides a reaction mixture that contains an isolated or recombinant β-1,3-N-acetylgalactosaminyltransferase polypeptide, that includes an amino acid sequence with at least 80%, 90% or 95% identity to SEQ ID NO:2. The reaction mixture is used to transfer a galactose moiety to an acceptor saccharide. A galactose moiety can be either, e.g., galactose or GalNAc. In a preferred embodiment, the galactose moiety is GalNAc. In another embodiment, the β-1,3-N-acetylgalactosaminyltransferase polypeptide comprises the amino acid sequence of SEQ ID NO:2.

In another aspect the present invention provides a method of producing a galactosylated product saccharide, the method comprising the steps of: a) contacting an acceptor substrate with a donor substrate comprising a galactose moiety and an isolated or recombinant β-1,3-N-acetylgalactosaminyltransferase polypeptide with at least 80%, 90%, or 95% identity to SEQ ID NO:2; and b) allowing transfer of a galactose moiety to the acceptor saccharide to occur, thereby producing the galactosylated product saccharide. In one embodiment, the β-1,3-N-acetylgalactosaminyltransferase polypeptide comprises the amino acid sequence of SEQ ID NO:2. In one preferred embodiment, the galactosylation method is performed at a commercial scale of production. In a further preferred embodiment, the acceptor substrate is a glycopeptide or glycoprotein.

In another aspect the present invention provides an isolated or recombinant β-1,3-N-acetylgalactosaminyltransferase nucleic acid molecule, that includes a nucleic acid sequence with at least 80%, 90, or 95% identity to SEQ ID NO:1, and that encodes a β-1,3-N-acetylgalactosaminyltransferase polypeptide that transfers a galactose moiety from a donor substrate to an acceptor substrate. A galactose moiety can be either, e.g., galactose or GalNAc. In a preferred embodiment, the galactose moiety is GalNAc. In another embodiment, the β-1,3-N-acetylgalactosaminyltransferase nucleic acid molecule comprises the amino acid sequence of SEQ ID NO:2. In a further embodiment, the invention provides an isolated or recombinant β-1,3-N-acetylgalactosaminyltransferase nucleic acid molecule that encodes SEQ ID NO:2.

In another aspect the present invention provides an expression vector that drives expression of an isolated or recombinant β-1,3-N-acetylgalactosaminyltransferase nucleic acid molecule that includes a nucleic acid sequence with at least 80%, 90, or 95% identity to SEQ ID NO:1, and that encodes a β-1,3-N-acetylgalactosaminyltransferase polypeptide that transfers a galactose moiety from a donor substrate to an acceptor substrate. A galactose moiety can be either, e.g., galactose or GalNAc. In a preferred embodiment, the galactose moiety is GalNAc. In another embodiment, the β-1,3-N-acetylgalactosaminyltransferase nucleic acid molecule comprises the amino acid sequence of SEQ ID NO:2. The invention also includes host cells that contain the expression vector and methods to make a β-1,3-N-acetylgalactosaminyltransferase polypeptide, by growing the host cell under conditions suitable for expression of the β-1,3-N-acetylgalactosaminyltransferase polypeptide.

BRIEF DESCRIPTION OF THE DRAWINGS

FIG. 3 provides an alignment between residues 5-167 of the CgtE protein (top line) [SEQ ID NO:3] and residues 1-161 of the glycosyl_transC2 consensus sequence (bottom line) [SEQ ID NO:4]. Identical residues are in bold and conserved residues are underlined.

DETAILED DESCRIPTION OF THE INVENTION

I. Introduction

Figure 1:
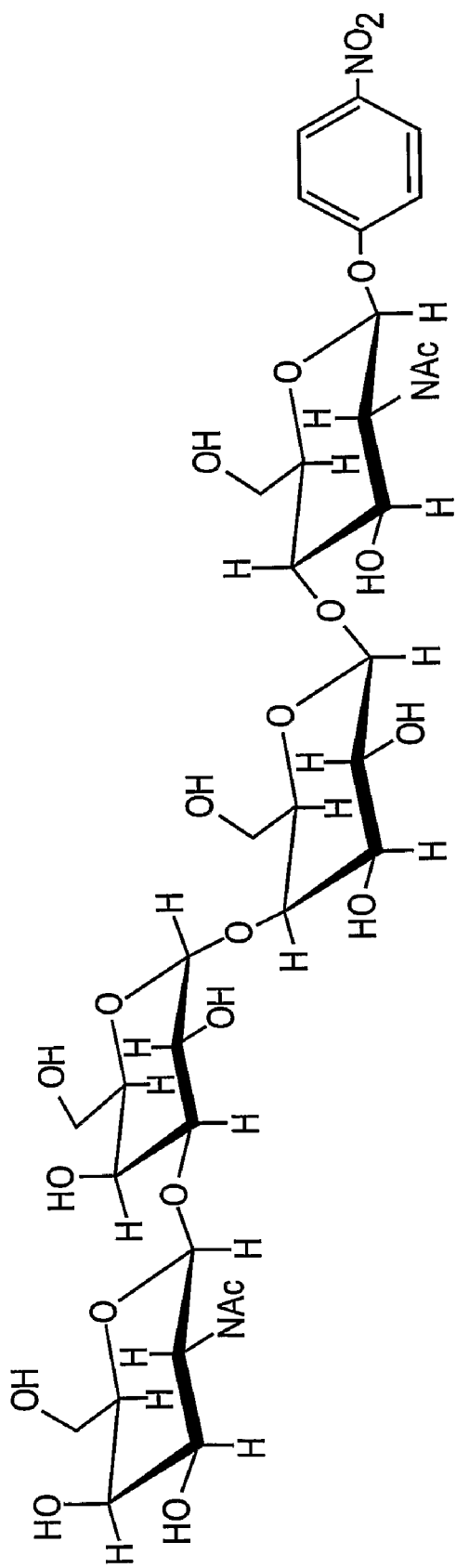
FIG. 1 provides the structure of GalNAcβ-1,3-Galα-1,4-Galβ-1,4-GlcNAc-p-nitrophenyl synthesized from Galα-1,4-Galβ-1,4-GlcNAc-p-nitrophenyl using CgtE.

The lipooligosaccharide (LOS) biosynthesis locus has been sequenced in various strains of *Campylobacter jejuni* as part of a project on the comparative genomics of this locus. See, e.g., Gilbert, et al., *J. Biol. Chem.* 275:3896-3906 (2000); Gilbert, et al., *J. Biol. Chem.* 277:327-337 (2002); and Gilbert, et al., in *Campylobacter: Molecular and Cellular Biology*. (Horizon Bioscience, Editors: J. M. Ketley and M. E. Konkel), Chapter 11 (2005). *C. jejuni* LIO87 is a type strain of the LIOR (heat labile) serotyping system. The organization of the LIO87 LOS locus (Class "D", GenBank accession number AF400669) is distinct from the majority of the *C. jejuni* LOS loci characterized so far (Classes "A", "B" and "C", Gilbert et al. 2002). The LOS locus from *C. jejuni* LIO87 lacks the cluster of genes involved in sialic acid biosynthesis and in the expression of LOS outer cores mimicking gangliosides. The *C. jejuni* LIO87 LOS locus includes 10 open reading frames (ORFs). Sequence homology searches indicated that four of these ORFs (ORFs #1, #2, #3 and #10) are involved in the biosynthesis of the inner core or the lipid A. It was not possible to infer the donor or acceptor specificities of the proteins encoded by the other six open reading frames based on sequence information.

The present invention demonstrates for the first time that the CgtE gene product has β-1,3-N-acetylgalactosaminyltransferase activity. In addition, the enzyme is also able to transfer galactose to an acceptor molecule. The CgtE protein can transfer either galactose or Gal NAc to a terminal galactose or GalNAc residue on an acceptor sugar.

II. Definitions

The following abbreviations are used herein:
Ara=arabinosyl;
Fru=fructosyl;
Fuc=fucosyl;
Gal=galactosyl;
GalNAc=N-acetylgalactosaminyl;
Glc=glucosyl;
GlcNAc=N-acetylglucosaminyl;
Man=mannosyl; and
NeuAc=sialyl (N-acetylneuraminyl).

An "acceptor substrate" or an "acceptor saccharide" for a glycosyltransferase, e.g., a CgtE polypeptide, is an oligosaccharide moiety that can act as an acceptor for a particular glycosyltransferase. When the acceptor substrate is contacted with the corresponding glycosyltransferase and sugar donor substrate, and other necessary reaction mixture components, and the reaction mixture is incubated for a sufficient period of time, the glycosyltransferase transfers sugar residues from the sugar donor substrate to the acceptor substrate. The acceptor substrate can vary for different types of a particular glycosyltransferase. Accordingly, the term "acceptor substrate" is taken in context with the particular glycosyltransferase of interest for a particular application. Acceptor substrates for GalNActransferases, e.g., CgtE from *C. jejuni* LIO87, and additional glycosyltransferases, are described herein.

A "donor substrate" for glycosyltransferases is an activated nucleotide sugar. Such activated sugars generally consist of uridine, guanosine, and cytidine monophosphate derivatives of the sugars (UMP, GMP and CMP, respectively) or diphosphate derivatives of the sugars (UDP, GDP and CDP, respectively) in which the nucleoside monophosphate or diphosphate serves as a leaving group. For example, a donor substrate for fucosyltransferases is GDP-fucose. Donor substrate for CgtE proteins include, e.g., UDP-GalNAc or UDP-Gal. Donor substrates for sialyltransferases, for example, are activated sugar nucleotides comprising the desired sialic acid. For instance, in the case of NeuAc, the activated sugar is CMP-NeuAc. Bacterial, plant, and fungal systems can sometimes use other activated nucleotide sugars.

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right. All oligosaccharides described herein are described with the name or abbreviation for the non-reducing saccharide (e.g., Gal), followed by the configuration of the glycosidic bond (α or β), the ring bond, the ring position of the reducing sugar involved in the bond, and then the name or abbreviation of the reducing saccharide (e.g., GlcNAc). The linkage between two sugars may be expressed, for example, as 2,3, 2→3, or (2,3). Each saccharide is a pyranose or furanose.

As used herein, a "galactose moiety" refers to a molecule that includes galactose or that can be derived from galactose. Galactose moieties are usually monosaccharides, e.g., galactose or GalNAc.

As used herein, a "galactosylated product saccharide" refers an oligosaccharide, a polysaccharide, or a carbohydrate moiety, either unconjugated or conjugated to a glycolipid or a glycoprotein, e.g., a biomolecule, that includes a galactose moiety. Any of the above galactose moieties can be used, e.g., galactose or GalNAc. In preferred embodiments the galactose moiety transferred by CgtE is GalNAc.

In some embodiments other sugar moieties, e.g., fucose, sialic acid, glucose, or GluNAc, are also added to the acceptor substrate through the action of additional glycosyltransferases to produce the galactosylated product saccharide. In some embodiments, the acceptor substrate comprises a galactose moiety and the CgtE protein is used to add an additional galactose moiety, making the galactosylated product saccharide.

The term "sialic acid" or "sialic acid moiety" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids: Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

Much of the nomenclature and general laboratory procedures required in this application can be found in Sambrook, et al., *Molecular Cloning: A Laboratory Manual* (2nd Ed.), Vol. 1-3, Cold Spring Harbor Laboratory, Cold Spring Harbor, N.Y., 1989. The manual is hereinafter referred to as "Sambrook et al."

The terms "CgtE from *C. jejuni* LIO87," "CgtE," or a nucleic acid encoding "CgtE from *C. jejuni* LIO87" or "CgtE" refer to nucleic acids and polypeptide polymorphic variants, alleles, mutants, and interspecies homologs that: (1) have an amino acid sequence that has at least 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to an amino acid sequence encoded by a CgtE from *C. jejuni* LIO87 nucleic acid (for a CgtE from *C. jejuni* LIO87 nucleic acid sequence, see, e.g., SEQ ID NO:1) or to an amino acid sequence of a CgtE from *C. jejuni* LIO87 protein (for a CgtE from *C. jejuni* LIO87 protein sequence, see, e.g., SEQ ID NO:2); (2) bind to antibodies, e.g., polyclonal antibodies, raised against an immunogen comprising an amino acid sequence of a CgtE from *C. jejuni* LIO87 protein, and conservatively modified variants thereof; (3) specifically hybridize under stringent hybridization conditions to an anti-sense strand corresponding to a nucleic acid sequence encoding a CgtE from *C. jejuni* LIO87 protein, and conservatively modified variants thereof; (4) have a nucleic acid sequence that has at least 90%, preferably at least 91%, 92%, 93%, 94%, 95%, 96%, 97%, 98%, 99%, or higher nucleotide sequence identity, preferably over a region of at least about 25, 50, 100, 200, 500, 1000, or more nucleotides, to a CgtE from *C. jejuni* LIO87 nucleic acid, e.g., SEQ ID NO:1, or a nucleic acid encoding the catalytic domain. Preferably the catalytic domain has at least 90%, preferably at least 91%, 92%, 93%, 94%, 95%, 96%, 97%, 98%, 99% amino acid identity to the CgtE from *C. jejuni* LIO87 catalytic domain of SEQ ID NO:2. A polynucleotide or polypeptide sequence is typically from a bacteria including, but not limited to, *Campylobacter, Haemophilus*, and *Pasteurella*. The nucleic acids and proteins of the invention include both naturally occurring or recombinant molecules. A CgtE from *C. jejuni* LIO87 protein typically has N-acetylgalactosaminyltransferase and galactosyltransferase activity. N-acetylgalactosaminyltransferase and galactosyltransferase assays can be performed according to methods known to those of skill in the art, using appropriate donor substrates and acceptor substrates, as described herein.

"Commercial scale" refers to gram scale production of a galactosylated product in a single reaction. In preferred embodiments, commercial scale refers to production of greater than about 50, 75, 80, 90, 100, 125, 150, 175, or 200 grams of galactosylated product.

As used herein, a "truncated CgtE polypeptide" or grammatical variants, refers to a CgtE polypeptide that has been manipulated to remove at least one amino acid residue, relative to a wild type CgtE polypeptide that occurs in nature, so long as the truncated CgtE polypeptide retains enzymatic activity. For example, a CgtE protein lacking the C-terminus 28 amino acids retains activity.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

Those of skill recognize that many amino acids can be substituted for one another in a protein without affecting the function of the protein, i.e., a conservative substitution can be the basis of a conservatively modified variant of a protein such as the disclosed CgtE proteins. An incomplete list of conservative amino acid substitutions follows. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V), Alanine (A); 6) Phenylalanine (F), Tyrosine (Y), Tryptophan (W); 7) Serine (S), Threonine (T), Cysteine (C); and 8) Cysteine (C), Methionine (M) (see, e.g., Creighton, *Proteins* (1984)).

The cells and methods of the invention are useful for producing a galactosylated product, generally by transferring a galactose moiety from a donor substrate to an acceptor molecule. The cells and methods of the invention are also useful for producing a galactosylated product sugar comprising additional sugar residues, generally by transferring a additional monosaccharide or a sulfate groups from a donor substrate to an acceptor molecule. The addition generally takes place at the non-reducing end of an oligosaccharide, polysaccharide (e.g., heparin, carragenin, and the like) or a carbohydrate moiety on a glycolipid or glycoprotein, e.g., a biomolecule. Biomolecules as defined here include but are not limited to biologically significant molecules such as carbohydrates, oligosaccharides, peptides (e.g., glycopeptides), proteins (e.g., glycoproteins), and lipids (e.g., glycolipids, phospholipids, sphingolipids and gangliosides).

The recombinant proteins of the invention can be constructed and expressed as a fusion protein with a molecular "purification tag" at one end, which facilitates purification or identification of the protein. Such tags can also be used for immobilization of a protein of interest during the glycosylation reaction. Suitable tags include "epitope tags," which are a protein sequence that is specifically recognized by an antibody. Epitope tags are generally incorporated into fusion proteins to enable the use of a readily available antibody to unambiguously detect or isolate the fusion protein. A "FLAG tag" is a commonly used epitope tag, specifically recognized by a monoclonal anti-FLAG antibody, consisting of the sequence AspTyrLysAspAspAsp AspLys [SEQ ID NO:5] or a substantially identical variant thereof. Other suitable tags are known to those of skill in the art, and include, for example, an affinity tag such as a hexahistidine peptide [SEQ ID NO:6], which will bind to metal ions such as nickel or cobalt ions or a myc tag. Proteins comprising purification tags can be purified using a binding partner that binds the purification tag, e.g., antibodies to the purification tag, nickel or cobalt ions or resins, and amylose, maltose, or a cyclodextrin. Purification tags also include maltose binding domains and starch binding domains. Purification of maltose binding domain proteins is known to those of skill in the art. Starch binding domains are described in WO 99/15636, herein incorporated by reference. Affinity purification of a fusion protein comprising a starch binding domain using a betacylodextrin (BCD)-derivatized resin is described in WO 2005/014779, published Feb. 17, 2005, herein incorporated by reference in its entirety.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof. The terms "nucleic acid", "nucleic acid sequence", and "polynucleotide" are used interchangeably herein.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant nucleic acid" refers to a nucleic acid that was artificially constructed (e.g., formed by linking two naturally-occurring or synthetic nucleic acid fragments). This term also applies to nucleic acids that are produced by replication or transcription of a nucleic acid that was artificially constructed. A "recombinant polypeptide" is expressed by transcription of a recombinant nucleic acid (i.e., a nucleic acid that is not native to the cell or that has been modified from its naturally occurring form), followed by translation of the resulting transcript.

A "heterologous polynucleotide" or a "heterologous nucleic acid", as used herein, is one that originates from a source foreign to the particular host cell, or, if from the same source, is modified from its original form. Thus, a heterologous glycosyltransferase gene in a prokaryotic host cell includes a glycosyltransferase gene that is endogenous to the particular host cell but has been modified. Modification of the heterologous sequence may occur, e.g., by treating the DNA with a restriction enzyme to generate a DNA fragment that is capable of being operably linked to a promoter. Techniques such as site-directed mutagenesis are also useful for modifying a heterologous sequence.

A "subsequence" refers to a sequence of nucleic acids or amino acids that comprise a part of a longer sequence of nucleic acids or amino acids (e.g., polypeptide) respectively.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

A "fusion CgtE polypeptide" or a "fusion glycosyltransferase polypeptide" of the invention is a polypeptide that contains a CgtE or glycosyltransferase catalytic domain and a second catalytic domain from an accessory enzyme (e.g., UDP-GalNAc 4' epimerase or a UDP-glucose 4'epimerase). The fusion polypeptide is capable of catalyzing the synthesis of a sugar nucleotide (e.g., UDP-GalNAc or UDP-Galactose) as well as the transfer of the sugar residue from the sugar nucleotide to an acceptor molecule. Typically, the catalytic domains of the fusion polypeptides will be at least substantially identical to those of glycosyltransferases and fusion proteins from which the catalytic domains are derived. In some embodiments, a CgtE polypeptide and an epimerase, e.g., UDP-GalNAc 4' UDP-glucose 4', polypeptide are fused to form a single polypeptide.

An "accessory enzyme," as referred to herein, is an enzyme that is involved in catalyzing a reaction that, for example, forms a substrate or other reactant for a glycosyltransferase reaction. An accessory enzyme can, for example, catalyze the formation of a nucleotide sugar that is used as a sugar donor moiety by a glycosyltransferase. An accessory enzyme can also be one that is used in the generation of a nucleotide triphosphate that is required for formation of a nucleotide sugar, or in the generation of the sugar which is incorporated into the nucleotide sugar.

A "catalytic domain" refers to a portion of an enzyme that is sufficient to catalyze an enzymatic reaction that is normally carried out by the enzyme. For example, a catalytic domain of a CgtE polypeptide will include a sufficient portion of the CgtE to transfer a galactose moiety from a sugar donor to an acceptor saccharide. A catalytic domain can include an entire enzyme, a subsequence thereof, or can include additional amino acid sequences that are not attached to the enzyme or subsequence as found in nature.

The term "isolated" refers to material that is substantially or essentially free from components which interfere with the activity of an enzyme. For cells, saccharides, nucleic acids, and polypeptides of the invention, the term "isolated" refers to material that is substantially or essentially free from components which normally accompany the material as found in its native state. Typically, isolated saccharides, proteins or nucleic acids of the invention are at least about 50%, 55%, 60%, 65%, 70%, 75%, 80% or 85% pure, usually at least about 90%, 91%, 92%, 93%, 94%, 95%, 96%, 97%, 98%, or 99% pure as measured by band intensity on a silver stained gel or other method for determining purity. Purity or homogeneity can be indicated by a number of means well known in the art, such as polyacrylamide gel electrophoresis of a protein or nucleic acid sample, followed by visualization upon staining. For certain purposes high resolution will be needed and HPLC or a similar means for purification utilized. For oligonucleotides, or other galactosylated products, purity can be determined using, e.g., thin layer chromatography, HPLC, or mass spectroscopy.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80% or 85%, most preferably at least 90%, 91%, 92%, 93%, 94%, 95%, 96%, 97%, 98%, or 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The phrase "hybridizing specifically to", refers to the binding, duplexing, or hybridizing of a molecule only to a particular nucleotide sequence under stringent conditions when that sequence is present in a complex mixture (e.g., total cellular) DNA or RNA.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na$^+$ ion, typically about 0.01 to 1.0 M Na$^+$ ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90-95° C. for 30-120 sec, an annealing phase lasting 30-120 sec, and an extension phase of about 72° C. for 1-2 min. Protocols and guidelines for low and high stringency amplification reactions are available, e.g., in Innis, et al. (1990) *PCR Protocols: A Guide to Methods and Applications* Academic Press, N.Y.

The phrases "specifically binds to" or "specifically immunoreactive with", when referring to an antibody refers to a binding reaction which is determinative of the presence of the protein or other antigen in the presence of a heterogeneous population of proteins, saccharides, and other biologics. Thus, under designated immunoassay conditions, the specified antibodies bind preferentially to a particular antigen and do not bind in a significant amount to other molecules present in the sample. Specific binding to an antigen under such conditions requires an antibody that is selected for its specificity for a particular antigen. A variety of immunoassay formats can be used to select antibodies specifically immunoreactive with a particular antigen. For example, solid-phase ELISA immunoassays are routinely used to select monoclonal antibodies specifically immunoreactive with an antigen. See Harlow and Lane (1988) *Antibodies, A Laboratory Manual*, Cold Spring Harbor Publications, New York, for a description of immunoassay formats and conditions that can be used to determine specific immunoreactivity.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. In a preferred embodiment, antibodies that specifically bind to a CgtE protein are produced. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F (ab)'$_2$, a dimer of Fab which itself is a light chain joined to $V_H$-$C_H$1 by a disulfide bond. The F (ab)'$_2$ may be reduced under mild conditions to break the disulfide linkage in the hinge region, thereby converting the F (ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* (3$^{rd}$ ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51

(1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

In one embodiment, the antibody is conjugated to an "effector" moiety. The effector moiety can be any number of molecules, including labeling moieties such as radioactive labels or fluorescent labels for use in diagnostic assays.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to IgE protein, polymorphic variants, alleles, orthologs, and conservatively modified variants, or splice variants, or portions thereof, can be selected to obtain only those polyclonal antibodies that are specifically immunoreactive with IgE proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

An "antigen" is a molecule that is recognized and bound by an antibody, e.g., peptides, carbohydrates, organic molecules, or more complex molecules such as glycolipids and glycoproteins. The part of the antigen that is the target of antibody binding is an antigenic determinant and a small functional group that corresponds to a single antigenic determinant is called a hapten.

A "label" is a composition detectable by spectroscopic, photochemical, biochemical, immunochemical, or chemical means. For example, useful labels include $^{32}P$, $^{125}I$, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:2 can be made detectable, e.g., by incorporating a radiolabel into the peptide, and used to detect antibodies specifically reactive with the peptide).

The term "immunoassay" is an assay that uses an antibody to specifically bind an antigen. The immunoassay is characterized by the use of specific binding properties of a particular antibody to isolate, target, and/or quantify the antigen.

The term "carrier molecule" means an immunogenic molecule containing antigenic determinants recognized by T cells. A carrier molecule can be a protein or can be a lipid. A carrier protein is conjugated to a polypeptide to render the polypeptide immunogenic. Carrier proteins include keyhole limpet hemocyanin, horseshoe crab hemocyanin, and bovine serum albumin.

The term "adjuvant" means a substance that nonspecifically enhances the immune response to an antigen. Adjuvants include Freund's adjuvant, either complete or incomplete; Titermax gold adjuvant; alum; and bacterial LPS.

The term "contacting" is used herein interchangeably with the following: combined with, added to, mixed with, passed over, incubated with, flowed over, etc.

III. CgtE Polypeptides

The CgtE polypeptides of the inventions comprise an amino acid sequence that is related to a conserved protein domain, the glycosyl_transf_2 domain, accession number PF00535. The glycosyltransferase 2 family of proteins is a group of proteins that were identified as such based on sequence comparisons. See, e.g., Campbell et al., *Biochem. J.* 326: 929-942 (1997). An alignment of amino acid residues 5-167 of CgtE with the sequence of the glycosyl_transf_2 domain is provided in FIG. 3. A glycosyl_transf_2-related domain is found in proteins that transfer sugar from UDP-glucose, UDP-N-acetyl-galactosamine, GDP-mannose or CDP-abequose, to a range of substrates including cellulose, dolichol phosphate and teichoic acids. See, e.g., www.sanger-.ac.uk/cgi-bin/Pfam/getacc?PF00535 and Coutinho, P. M. & Henrissat, B. (1999) Carbohydrate-Active Enzymes server at URL: afmb.cnrs-mrs.fr/CAZY/.

At present 2395 proteins that contain a glycosyl_transf_2-related domain have been identified in eukaryotes, e.g., mammals, metazoans, amphibians, arthropods, plants, fungi, and bacteria. The glycosyl_transf_2-related domain corresponds to a three dimensional fold that is believed to occur in each of the proteins, and thus, a large number of sequences are available for comparison of sequence and structure, in addition to the glycosyl_transf_2 domain. See e.g., www.sanger-.ac.uk/cgi-bin/Pfam/getacc?PF00535. The structure of the conserved three dimensional fold is known and available for structure function analysis. See, e.g., protein databank (PDB) numbers 1h71, 1h7q, 1qgq, 1qg8, and 1qgs; and Tarbouriech, et al., *J. Mol. Biol.* 314:655-(2001).

Computer programs that compare previously unknown sequences such as the CgtE amino acid sequences to known sequences, such as the glycosyl_transf_2 domain, are freely available to those of skill. One such program is Cn3D which can be downloaded from www.ncbi.nlm.nih.gov/Structure/CN3D/cn3d.shtml. Cn3D correlates structure and sequence information: for example, a scientist can quickly find the residues in a crystal structure that correspond to known disease mutations, or conserved active site residues from a family of sequence homologs. Cn3D displays structure-structure alignments along with their structure-based sequence alignments, to emphasize what regions of a group of related proteins are most conserved in structure and sequence. Thus, using a program such as Cn3D, those of skill can identify conserved residues in the glycosyl_transf_2-related domain of CgtE and moreover, can predict changes in amino acid residues that would likely not effect activity of the protein. In addition, using the Cn3D program, those of skill could also predict changes in amino acid residues that would be detrimental to CgtE activity and avoid them.

At a minimum, the CgtE polypeptides comprise amino acid residues 5-167 of SEQ ID NO:2, i.e., the glycosyl_transf_2-related domain as described above.

IV. Isolation of Nucleic Acids Encoding CgtE Polypeptides

Nucleic acids that encode CgtE polypeptides include nucleic acids that encode the CgtE polypeptides described above, i.e., SEQ ID NO:2, and conservatively modified variants of that sequence. The CgtE polypeptides of the invention catalyze the transfer of a galactose moiety from a donor substrate to an acceptor substrate.

Nucleic acids that encode additional CgtE polypeptides based on the information disclosed herein, and methods of obtaining such nucleic acids, are known to those of skill in the art. Suitable nucleic acids (e.g., cDNA, genomic, or subsequences (probes)) can be cloned, or amplified by in vitro methods such as the polymerase chain reaction (PCR), the ligase chain reaction (LCR), the transcription-based amplification system (TAS), or the self-sustained sequence replication system (SSR). A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864.

A DNA that encodes a CgtE polypeptide, or a subsequences thereof, can be prepared by any suitable method described above, including, for example, cloning and restriction of appropriate sequences with restriction enzymes. In one preferred embodiment, nucleic acids encoding CgtE polypeptides are isolated by routine cloning methods. A nucleotide sequence of a CgtE polypeptide as provided in, for example, SEQ ID NO:2, can be used to provide probes that specifically hybridize to a gene encoding a CgtE polypeptide in a genomic DNA sample; or to an mRNA, encoding a CgtE polypeptide comprising, in a total RNA sample (e.g., in a Southern or Northern blot). Once the target nucleic acid encoding a CgtE polypeptide is identified, it can be isolated according to standard methods known to those of skill in the art (see, e.g., Sambrook et al. (1989) *Molecular Cloning: A Laboratory Manual, 2nd Ed., Vols.* 1-3, Cold Spring Harbor Laboratory; Berger and Kimmel (1987) *Methods in Enzymology, Vol.* 152: *Guide to Molecular Cloning Techniques*, San Diego Academic Press, Inc.; or Ausubel et al. (1987) *Current Protocols in Molecular Biology*, Greene Publishing and Wiley-Interscience, New York). Further, the isolated nucleic acids can be cleaved with restriction enzymes to create nucleic acids encoding the full-length CgtE polypeptide, or subsequences thereof, e.g., containing subsequences encoding at least a subsequence of a catalytic domain of a CgtE polypeptide B. These restriction enzyme fragments, encoding a CgtE polypeptide or subsequences thereof, may then be ligated, for example, to produce a nucleic acid encoding a CgtE protein.

A nucleic acid encoding a CgtE polypeptide, or a subsequence thereof, can be characterized by assaying for the expressed product. Assays based on the detection of the physical, chemical, or immunological properties of the expressed protein can be used. For example, one can identify a cloned CgtE nucleic acid B, by the ability of a protein encoded by the nucleic acid to catalyze the transfer of a galactose moiety from a donor substrate to an acceptor substrate. In one method, capillary electrophoresis is employed to detect the reaction products. This highly sensitive assay involves using either saccharide or disaccharide aminophenyl derivatives which are labeled with fluorescein as described in Wakarchuk et al. (1996) *J. Biol. Chem.* 271 (45): 28271-276. To assay for CgtE activity, Galα-Lac-FCHASE or GalNAc-α-FCHASE is used as a substrate. The reaction products of other glycosyltransferases can be detected using capillary electrophoresis, e.g., to assay for a *Neisseria* lgtC enzyme, either FCHASE-AP-Lac or FCHASE-AP-Gal can be used, whereas for the *Neisseria* lgtB enzyme an appropriate reagent is FCHASE-AP-GlcNAc (Wakarchuk, supra). To assay for α2,8-sialyltransferase, GM3-FCHASE is used as a substrate. See, e.g., U.S. Pat. No. 6,503,744, which is herein incorporated by reference. Other methods for detection of oligosaccharide reaction products include thin layer chromatography and GC/MS and are disclosed in U.S. Pat. No. 6,503,744, which is herein incorporated by reference.

Also, a nucleic acid encoding a CgtE polypeptide, or a subsequence thereof, can be chemically synthesized. Suitable methods include the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill recognizes that while chemical synthesis of DNA is often limited to sequences of about 100 bases, longer sequences may be obtained by the ligation of shorter sequences.

Nucleic acids encoding CgtE polypeptides, or subsequences thereof, can be cloned using DNA amplification methods such as polymerase chain reaction (PCR). Thus, for example, the nucleic acid sequence or subsequence is PCR amplified, using a sense primer containing one restriction enzyme site (e.g., NdeI) and an antisense primer containing another restriction enzyme site (e.g., HindIII). This will produce a nucleic acid encoding the desired CgtEe polypeptide or a subsequence and having terminal restriction enzyme sites. This nucleic acid can then be easily ligated into a vector containing a nucleic acid encoding the second molecule and having the appropriate corresponding restriction enzyme sites. Suitable PCR primers can be determined by one of skill in the art using the sequence information provided in GenBank or other sources. Appropriate restriction enzyme sites can also be added to the nucleic acid encoding the CgtE protein or a protein subsequence thereof by site-directed mutagenesis. The plasmid containing the CgtE protein-encoding nucleotide sequence or subsequence is cleaved with the appropriate restriction endonuclease and then ligated into an appropriate vector for amplification and/or expression according to standard methods. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al., eds) Academic Press Inc. San Diego, Calif. (1990) (Innis); Arnheim & Levinson (Oct. 1, 1990) *C&EN* 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.,* 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89: 117.

Some nucleic acids encoding bacterial CgtE proteins can be amplified using PCR primers based on the sequence of CgtE nucleic acids disclosed herein. Examples of PCR primers that can be used to amplify nucleic acid that encode CgtE proteins include the following primer pairs:

```
5-prime primer with NdeI site: CJ-640:
                                            [SEQ ID NO: 7]
TTTAAGAAAACATATGCCTAAAATTTCAATCATC 3-prime primer with SalI site: CJ-641:
                                            [SEQ ID NO: 8]
GGTAATCTAGTCGACAATTATAACACATTC
```

In some bacteria, nucleic acids encoding CgtE protein can be isolated by amplifying a specific chromosomal locus, e.g., the LOS locus of *C. jejuni*, and then identifying a CgtE nucleic acid typically found at that locus (see, e.g., U.S. Pat. No. 6,503,744). Examples of PCR primers that can be used to amplify an LOS locus comprising nucleic acids encoding a CgtE protein include the following primer pairs:

```
CJ42: Primer in heptosylTase-II
                                          [SEQ ID NO: 9]
5' GC CAT TAC CGT ATC GCC TAA CCA GG 3' 25 mer CJ43: Primer in heptosylTase-I
                                          [SEQ ID NO: 10]
5' AAA GAA TAC GAA TTT GCT AAA GAG G 3' 25 mer
```

Other physical properties of a recombinant CgtE polypeptide expressed from a particular nucleic acid, can be compared to properties of known CgtE polypeptides to provide another method of identifying suitable sequences or domains of the CgtE polypeptide that are determinants of acceptor substrate specificity and/or catalytic activity. Alternatively, a putative CgtE polypeptide or recombinant CgtE polypeptide can be mutated, and its role as a glycosyltransferase, or the role of particular sequences or domains established by detecting a variation in the structure of a carbohydrate normally produced by the unmutated, naturally-occurring, or control CgtE polypeptide. Those of skill will recognize that mutation or modification of CgtE polypeptides of the invention can be facilitated by molecular biology techniques to manipulate the nucleic acids encoding the CgtE polypeptides, e.g., PCR.

Functional domains of newly identified CgtE polypeptides can be identified by using standard methods for mutating or modifying the polypeptides and testing them for activities such as acceptor substrate activity and/or catalytic activity, as described herein. The functional domains of the various CgtEe polypeptides can be used to construct nucleic acids encoding CgtE polypeptides and the functional domains of one or more CgtE polypeptides. These multi-CgtE fusion proteins can then be tested for the desired acceptor substrate or catalytic activity.

In an exemplary approach to cloning nucleic acids encoding CgtE proteins, the known nucleic acid or amino acid sequences of cloned CgtE polypeptides are aligned and compared to determine the amount of sequence identity between various CgtE polypeptides. This information can be used to identify and select protein domains that confer or modulate CgtE activities, e.g., acceptor substrate activity and/or catalytic activity based on the amount of sequence identity between the CgtE proteins of interest. For example, domains having sequence identity between the CgtE proteins of interest, and that are associated with a known activity, can be used to construct CgtE proteins containing that domain, and having the activity associated with that domain (e.g., acceptor substrate specificity and/or catalytic activity).

V. Expression of CgtE Polypeptides in Host Cells

CgtE proteins of the invention can be expressed in a variety of host cells, including *E. coli*, other bacterial hosts, and yeast. The host cells are preferably microorganisms, such as, for example, yeast cells, bacterial cells, or filamentous fungal cells. Examples of suitable host cells include, for example, *Azotobacter* sp. (e.g., *A. vinelandii*), *Pseudomonas* sp., *Rhizobium* sp., *Erwinia* sp., *Escherichia* sp. (e.g., *E. coli*), *Bacillus, Pseudomonas, Proteus, Salmonella, Serratia, Shigella, Rhizobia, Vitreoscilla, Paracoccus* and *Klebsiella* sp., among many others. The cells can be of any of several genera, including *Saccharomyces* (e.g., *S. cerevisiae*), *Candida* (e.g., *C. utilis, C. parapsilosis, C. krusei, C. versatilis, C. lipolytica, C. zeylanoides, C. guilliermondii, C. albicans*, and *C. humicola*), *Pichia* (e.g., *P. farinosa* and *P. ohmeri*), *Torulopsis* (e.g., *T. candida, T. sphaerica, T. xylinus, T. famata*, and *T. versatilis*), *Debaryomyces* (e.g., *D. subglobosus, D. cantarelli, D. globosus, D. hansenii*, and *D. japonicus*), *Zygosaccharomyces* (e.g., *Z. rouxii* and *Z. bailii*), *Kluyveromyces* (e.g., *K. marxianus*), *Hansenula* (e.g., *H. anomala* and *H. jadinii*), and *Brettanomyces* (e.g., *B. lambicus* and *B. anomalus*). Examples of useful bacteria include, but are not limited to, *Escherichia, Enterobacter, Azotobacter, Erwinia, Klebsielia, Bacillus, Pseudomonas, Proteus*, and *Salmonella.*

Once expressed in a host cell, the CgtE polypeptides can be used to produced galactosylated products. For example, the CgtE polypeptides can be isolated using standard protein purification techniques and used in in vitro reactions described herein to make galactosylated products. Partially purified CgtE polypeptides can also be used in in vitro reactions to make galactosylated products as can the permeabilized host cells. The host cells can also be used in an in vivo system (e.g., fermentative production) to produce galactosylated products.

Typically, the polynucleotide that encodes the CgtE polypeptides is placed under the control of a promoter that is functional in the desired host cell. An extremely wide variety of promoters are well known, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the invention provides expression cassettes into which the nucleic acids that encode fusion proteins are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res.* (1980) δ: 4057), the tac promoter (DeBoer, et al., *Proc. Natl. Acad. Sci. U.S.A.* (1983) 80:21-25); and the lambda-derived $P_L$ promoter and N-gene ribosome binding site (Shimatake et al., *Nature* (1981) 292: 128). The particular promoter system is not critical to the invention, any available promoter that functions in prokaryotes can be used.

For expression of CgtE proteins in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in *Bacillus* in addition to *E. coli*.

A ribosome binding site (RBS) is conveniently included in the expression cassettes of the invention. An RBS in *E. coli*, for example, consists of a nucleotide sequence 3-9 nucleotides in length located 3-11 nucleotides upstream of the initiation codon (Shine and Dalgarno, *Nature* (1975) 254: 34; Steitz, *In Biological regulation and development: Gene expression* (ed. R. F. Goldberger), vol. 1, p. 349, 1979, Plenum Publishing, NY).

For expression of the CgtE proteins in yeast, convenient promoters include GAL1-10 (Johnson and Davies (1984) *Mol. Cell. Biol.* 4:1440-1448) ADH2 (Russell et al. (1983) *J. Biol. Chem.* 258:2674-2682), PHO5 (*EMBO J.* (1982) 6:675-680), and MFα (Herskowitz and Oshima (1982) in *The Molecular Biology of the Yeast Saccharomyces* (eds. Strathern, Jones, and Broach) Cold Spring Harbor Lab., Cold Spring Harbor, N.Y., pp. 181-209). Another suitable promoter for use in yeast is the ADH2/GAPDH hybrid promoter as described in Cousens et al., *Gene* 61:265-275 (1987). For filamentous fungi such as, for example, strains of the fungi *Aspergillus* (McKnight et al., U.S. Pat. No. 4,935,349), examples of useful promoters include those derived from *Aspergillus nidulans* glycolytic genes, such as the ADH3 promoter (McKnight et al., *EMBO J.* 4: 2093 2099 (1985)) and the tpiA promoter. An example of a suitable terminator is the ADH3 terminator (McKnight et al.).

Either constitutive or regulated promoters can be used in the present invention. Regulated promoters can be advantageous because the host cells can be grown to high densities before expression of the fusion proteins is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, which allow one to control the timing of expression of the glycosyltransferase or enzyme involved in nucleotide sugar synthesis. For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene* 25: 167; de Boer et al. (1983) *Proc. Nat'l. Acad. Sci. USA* 80: 21), and the bacteriophage T7 promoter (Studier et al. (1986) *J. Mol. Biol.*; Tabor et al. (1985) *Proc. Nat'l. Acad. Sci. USA* 82:1074-8). These promoters and their use are discussed in Sambrook et al., supra. A particularly preferred inducible promoter for expression in prokaryotes is a dual promoter that includes a tac promoter component linked to a promoter component obtained from a gene or genes that encode enzymes involved in galactose metabolism (e.g., a promoter from a UDPgalactose 4-epimerase gene (ga/E)). The dual tac-gal promoter, which is described in PCT Patent Application Publ. No. WO98/20111, A construct that includes a polynucleotide of interest operably linked to gene expression control signals that, when placed in an appropriate host cell, drive expression of the polynucleotide is termed an "expression cassette." Expression cassettes that encode the fusion proteins of the invention are often placed in expression vectors for introduction into the host cell. The vectors typically include, in addition to an expression cassette, a nucleic acid sequence that enables the vector to replicate independently in one or more selected host cells. Generally, this sequence is one that enables the vector to replicate independently of the host chromosomal DNA, and includes origins of replication or autonomously replicating sequences. Such sequences are well known for a variety of bacteria. For instance, the origin of replication from the plasmid pBR322 is suitable for most Gram-negative bacteria. Alternatively, the vector can replicate by becoming integrated into the host cell genomic complement and being replicated as the cell undergoes DNA replication. A preferred expression vector for expression of the enzymes is in bacterial cells is pTGK, which includes a dual tac-gal promoter and is described in PCT Patent Application Publ. NO. WO98/20111.

The construction of polynucleotide constructs generally requires the use of vectors able to replicate in bacteria. A plethora of kits are commercially available for the purification of plasmids from bacteria (see, for example, EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, and used to transfect cells. Cloning in *Streptomyces* or *Bacillus* is also possible.

Selectable markers are often incorporated into the expression vectors used to express the polynucleotides of the invention. These genes can encode a gene product, such as a protein, necessary for the survival or growth of transformed host cells grown in a selective culture medium. Host cells not transformed with the vector containing the selection gene will not survive in the culture medium. Typical selection genes encode proteins that confer resistance to antibiotics or other toxins, such as ampicillin, neomycin, kanamycin, chloramphenicol, or tetracycline. Alternatively, selectable markers may encode proteins that complement auxotrophic deficiencies or supply critical nutrients not available from complex media, e.g., the gene encoding D-alanine racemase for Bacilli. Often, the vector will have one selectable marker that is functional in, e.g., *E. coli*, or other cells in which the vector is replicated prior to being introduced into the host cell. A number of selectable markers are known to those of skill in the art and are described for instance in Sambrook et al., supra.

Construction of suitable vectors containing one or more of the above listed components employs standard ligation techniques as described in the references cited above. Isolated plasmids or DNA fragments are cleaved, tailored, and re-ligated in the form desired to generate the plasmids required. To confirm correct sequences in plasmids constructed, the plasmids can be analyzed by standard techniques such as by restriction endonuclease digestion, and/or sequencing according to known methods. Molecular cloning techniques to achieve these ends are known in the art. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kimmel, *Guide to Molecular Cloning Techniques, Methods in Enzymology*, Volume 152, Academic Press, Inc., San Diego, Calif. (Berger); and Current Protocols in Molecular Biology, F. M. Ausubel et al., eds., *Current Protocols*, a joint venture between Greene Publishing Associates, Inc. and John Wiley & Sons, Inc., (1998 Supplement) (Ausubel).

A variety of common vectors suitable for use as starting materials for constructing the expression vectors of the invention are well known in the art. For cloning in bacteria, common vectors include pBR322 derived vectors such as pBLUESCRIPT™, and k-phage derived vectors. In yeast, vectors include Yeast Integrating plasmids (e.g., YIp5) and Yeast Replicating plasmids (the YRp series plasmids) and pGPD-2. Expression in mammalian cells can be achieved using a variety of commonly available plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses).

The methods for introducing the expression vectors into a chosen host cell are not particularly critical, and such methods are known to those of skill in the art. For example, the expression vectors can be introduced into prokaryotic cells, including *E. coli*, by calcium chloride transformation, and into eukaryotic cells by calcium phosphate treatment or electroporation. Other transformation methods are also suitable.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297-16302.

The CgtE polypeptides can be expressed intracellularly, or can be secreted from the cell. Intracellular expression often results in high yields. If necessary, the amount of soluble, active fusion protein may be increased by performing refolding procedures (see, e.g., Sambrook et al., supra.; Marston et al., *Bio/Technology* (1984) 2: 800; Schoner et al., *Bio/Technology* (1985) 3: 151). In embodiments in which the CgtE polypeptides are secreted from the cell, either into the periplasm or into the extracellular medium, the DNA sequence is linked to a cleavable signal peptide sequence. The signal sequence directs translocation of the fusion protein through the cell membrane. An example of a suitable vector for use in *E. coli* that contains a promoter-signal sequence unit is pTA1529, which has the *E. coli* phoA promoter and signal sequence (see, e.g., Sambrook et al., supra.; Oka et al., *Proc. Natl. Acad. Sci. USA* (1985) 82: 7212; Talmadge et al., *Proc. Natl. Acad. Sci. USA* (1980) 77: 3988; Takahara et al., *J. Biol. Chem.* (1985) 260: 2670). In another embodiment, the CgtE proteins are fused to a subsequence of protein A or bovine serum albumin (BSA), for example, to facilitate purification, secretion, or stability.

The CgtE polypeptides of the invention can also be further linked to other bacterial proteins. This approach often results in high yields, because normal prokaryotic control sequences direct transcription and translation. In *E. coli*, lacZ fusions are often used to express heterologous proteins. Suitable vectors are readily available, such as the pUR, pEX, and pMR100 series (see, e.g., Sambrook et al., supra.). For certain applications, it may be desirable to cleave the non-glycosyltransferase and/or accessory enzyme amino acids from the fusion protein after purification. This can be accomplished by any of several methods known in the art, including cleavage by cyanogen bromide, a protease, or by Factor $X_a$ (see, e.g., Sambrook et al., supra.; Itakura et al., *Science* (1977) 198: 1056; Goeddel et al., *Proc. Natl. Acad. Sci. USA* (1979) 76: 106; Nagai et al., *Nature* (1984) 309: 810; Sung et al., *Proc. Natl. Acad. Sci. USA* (1986) 83: 561). Cleavage sites can be engineered into the gene for the fusion protein at the desired point of cleavage.

More than one recombinant protein may be expressed in a single host cell by placing multiple transcriptional cassettes in a single expression vector, or by utilizing different selectable markers for each of the expression vectors which are employed in the cloning stategy.

A suitable system for obtaining recombinant proteins from *E. coli* which maintains the integrity of their N-termini has been described by Miller et al. *Biotechnology* 7:698-704 (1989). In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal reside.

VI. Purification of CgtE Polypeptides

The CgtE proteins of the present invention can be expressed as intracellular proteins or as proteins that are secreted from the cell, and can be used in this form, in the methods of the present invention. For example, a crude cellular extract containing the expressed intracellular or secreted CgtE polypeptide can used in the methods of the present invention.

Alternatively, the CgtE polypeptide can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol. 182: Guide to Protein Purification.*, Academic Press, Inc. N.Y. (1990)). Substantially pure compositions of at least about 70, 75, 80, 85, 90% homogeneity are preferred, and 92, 95, 98 to 99% or more homogeneity are most preferred. The purified proteins may also be used, e.g., as immunogens for antibody production.

To facilitate purification of the CgtE polypeptides of the invention, the nucleic acids that encode the proteins can also include a coding sequence for an epitope or "tag" for which an affinity binding reagent is available, i.e. a purification tag. Examples of suitable epitopes include the myc and V-5 reporter genes; expression vectors useful for recombinant production of fusion proteins having these epitopes are commercially available (e.g., Invitrogen (Carlsbad CA) vectors pcDNA3.1/Myc-His and pcDNA3.1/V5-His are suitable for expression in mammalian cells). Additional expression vectors suitable for attaching a tag to the CgtE polypeptide of the invention, and corresponding detection systems are known to those of skill in the art, and several are commercially available (e.g., FLAG" (Kodak, Rochester NY). Another example of a suitable tag is a polyhistidine sequence which is capable of binding to metal chelate affinity ligands. Typically, six adjacent histidines are used, although one can use more or less than six. Suitable metal chelate affinity ligands that can serve as the binding moiety for a polyhistidine tag include nitrilotriacetic acid (NTA) (Hochuli, E. (1990) "Purification of recombinant proteins with metal chelating adsorbents" In Genetic Engineering: Principles and Methods, J.K. Setlow, Ed., Plenum Press, NY; commercially available from Qiagen (Santa Clarita, Calif.)). Other purification or epitope tags include, e.g., AU1, AU5, DDDDK (EC5) [SEQ ID NO:11], E tag, E2 tag, Glu-Glu, a 6 residue peptide, EYMPME [SEQ ID NO:12], derived from the Polyoma middle T protein, HA, HSV, IRS, KT3, S tage, S1 tag, T7 tag, V5 tag, VSV-G, β-galactosidase, Gal4, green fluorescent protein (GFP), luciferase, protein C, protein A, cellulose binding protein, GST (glutathione S transferase), a step-tag, Nus-S, PPI-ases, Pfg 27, calmodulin binding protein, dsb A and fragments thereof, and granzyme B. Epitope peptides and antibodies that bind specifically to epitope sequences are commercially available from, e.g., Covance Research Products, Inc.; Bethyl Laboratories, Inc.; Abcam Ltd.; and Novus Biologicals, Inc.

Purification tags also include maltose binding domains and starch binding domains. Proteins comprising purification tags can be purified using a binding partner that binds the purification tag, e.g., antibodies to the purification tag, nickel or cobalt ions or resins, and amylose, maltose, or a cyclodextrin. Purification tags also include starch binding domains, E. coli thioredoxin domains (vectors and antibodies commercially available from e.g., Santa Cruz Biotechnology, Inc. and Alpha Diagnostic International, Inc.), and the carboxy-terminal half of the SUMO protein (vectors and antibodies commercially available from e.g., Life Sensors Inc.). Starch binding domains, such as a maltose binding domain from E. coli and SBD (starch binding domain) from an amylase of A. niger, are described in WO 99/15636, herein incorporated by reference. Affinity purification of a fusion protein comprising a starch binding domain using a betacyclodextrin (BCD)-derivatized resin is described in WO 2005/014779, published Feb. 17, 2005, herein incorporated by reference in its entirety. In some embodiments, a CgtE polypeptide comprises more than one purification or epitope tag.

Other haptens that are suitable for use as tags are known to those of skill in the art and are described, for example, in the Handbook of Fluorescent Probes and Research Chemicals (6th Ed., Molecular Probes, Inc., Eugene Oreg.). For example, dinitrophenol (DNP), digoxigenin, barbiturates (see, e.g., U.S. Pat. No. 5,414,085), and several types of fluorophores are useful as haptens, as are derivatives of these compounds. Kits are commercially available for linking haptens and other moieties to proteins and other molecules. For example, where the hapten includes a thiol, a heterobifunctional linker such as SMCC can be used to attach the tag to lysine residues present on the capture reagent.

One of skill would recognize that modifications can be made to the catalytic or functional domains of the CgtE polypeptide without diminishing their biological activity. Some modifications may be made to facilitate the cloning, expression, or incorporation of the catalytic domain into a fusion protein. Such modifications are well known to those of skill in the art and include, for example, the addition of codons at either terminus of the polynucleotide that encodes the catalytic domain to provide, for example, a methionine added at the amino terminus to provide an initiation site, or additional amino acids (e.g., poly His) placed on either terminus to create conveniently located restriction enzyme sites or termination codons or purification sequences.

VII. Fusion CgtE Proteins

In some embodiments, the recombinant cells of the invention express fusion proteins that have more than one enzymatic activity that is involved in synthesis of a desired galactosylated oligosaccharide. The fusion polypeptides can be composed of, for example, a CgtE polypeptide that is joined to a an accessory enzyme, e.g., [UDP-GalNAc 4' epimerase or a UDP-glucose 4'epimerase. Fusion proteins can also be made using catalytic domains or other truncations of the enzymes. For example, a polynucleotide that encodes a CgtE polypeptide can be joined, in-frame, to a polynucleotide that encodes, e.g., a UDP-GalNAc 4' epimerase or a UDP-glucose 4'epimerase. The resulting fusion protein can then catalyze not only the synthesis of the activated galactose or GalNAc molecule, but also the transfer of the galacotse moiety to the acceptor molecule. The fusion protein can be two or more galacotse cycle enzymes linked into one expressible nucleotide sequence. The fusion CgtE polypeptides of the present invention can be readily designed and manufactured utilizing various recombinant DNA techniques well known to those skilled in the art. Exemplary fusion proteins are described in PCT Patent Application PCT/CA98/01180, which was published as WO99/31224 on Jun. 24, 1999 and which discloses CMP-sialic acid synthase from Neisseria fused with an α2,3-sialyltransferase from Neisseria. In some embodiments, more that one fusion CgtE polypeptide is expressed in the cell. Fusion protein can also comprise purification or epitope tags as described herein.

VIII. Donor Substrates and Acceptor Substrates

Suitable donor substrates used by the CgtE polypeptides and other glycosyltransferases in the methods of the invention include, but are not limited to, UDP-Glc, UDP-GlcNAc, UDP-Gal, UDP-GalNAc, GDP-Man, GDP-Fuc, UDP-GlcUA, and CMP-sialic acid and other activated sialic acid moieties. Guo et al., Applied Biochem. and Biotech. 68: 1-20 (1997)

Typically, acceptor substrates include a terminal galactose or GalNAc residue for addition of a galactose or GalNAc residue by a β1,3 linkage. Examples of suitable acceptors include a terminal Gal that is linked to GlcNAc or Glc by a β1,4 linkage, and a terminal Gal that is β1,3-linked to either GlcNAc or GalNAc. Suitable acceptors, include, for example, galactosyl acceptors such as Galβ1,4GlcNAc, Galβ1,4GalNAc, Galβ1,3GalNAc, lacto-N-tetraose, Galβ1,3GlcNAc, Galβ1,3Ara, Galβ1,6GlcNAc, Galβ1,4Glc (lactose), and other acceptors known to those of skill in the art. The terminal residue to which the galactose moiety is attached can itself be attached to, for example, H, a saccharide, oligosaccharide, or an aglycone group having at least one carbohydrate atom. In some embodiments, the acceptor residue is a portion of an oligosaccharide that is attached to a peptide, a protein, a lipid, or a proteoglycan, for example.

Suitable acceptor substrates used by the CgtE polypeptides and methods of the invention include, but are not limited to, polysaccharides and oligosaccharides. The CgtE polypeptides described herein can also be used in multienzyme systems to produce a desired product from a convenient starting material.

Suitable acceptor substrates used by the CgtE polypeptides and methods of the invention include, but are not limited to, proteins, lipids, gangliosides and other biological structures (e.g., whole cells) that can be modified by the methods of the invention. These acceptor substrates will typically comprise the polysaccharide or oligosaccharide molecules described above. Exemplary structures, which can be modified by the methods of the invention include any a of a number glycolipids, glycoproteins and carbohydrate structures on cells known to those skilled in the art as set forth is Table 1.

TABLE 1

| Hormones and Growth Factors |
| --- |
| G-CSF |
| GM-CSF |
| TPO |
| EPO |
| EPO variants |
| α-TNF |
| Leptin |
| Enzymes and Inhibitors |
| t-PA |
| t-PA variants |
| Urokinase |
| Factors VII, VIII, IX, X |
| DNase |
| Glucocerebrosidase |
| Hirudin |
| α1 antitrypsin |
| Antithrombin III |

TABLE 1-continued

Cytokines and Chimeric Cytokines

Interleukin-1 (IL-1), 1B, 2, 3, 4
Interferon-α (IFN-α)
IFN-α-2b
IFN-β
IFN-γ
Chimeric diptheria toxin-IL-2

Receptors and Chimeric Receptors

CD4
Tumor Necrosis Factor (TNF) receptor
Alpha-CD20
MAb-CD20
MAb-alpha-CD3
MAb-TNF receptor
MAb-CD4
PSGL-1
MAb-PSGL-1
Complement
GlyCAM or its chimera
N-CAM or its chimera
LFA-3
CTLA-IV Monoclonal Antibodies (Immunoglobulins)

MAb-anti-RSV
MAb-anti-IL-2 receptor
MAb-anti-CEA
MAb-anti-platelet IIb/IIIa receptor
MAb-anti-EGF
MAb-anti-Her-2 receptor Cells Red blood cells
White blood cells (e.g., T cells, B cells,
dendritic cells, macrophages, NK cells,
neutrophils, monocytes and the like
Stem cells The present invention provides CgtE polypeptides that are selected for their ability to produce oligosaccharides, glycoproteins and glycolipids having desired oligosaccharide moieties. Similarly, if present, accessory enzymes are chosen based on an desired activated sugar substrate or on a sugar found on the product oligosaccharide.

For synthesis of glycoproteins, one can readily identify suitable CgtE polypeptides by reacting various amounts of a CgtE polypeptide of interest (e.g., 0.01-100 mU/mg protein) with a glycoprotein (e.g., at 1-10 mg/ml) to which is linked an oligosaccharide that has a potential acceptor site for glycosylation by the CgtE protein of interest. The abilities of the recombinant CgtE proteins of the present invention to add a sugar residue at the desired acceptor site are compared, and a CgtE polypeptide having the desired property (e.g., acceptor substrate specificity or catalytic activity) is selected.

In general, the efficacy of the enzymatic synthesis of oligosaccharides, glycoproteins, and glycolipids, having desired galactosylated oligosaccharide moieties, can be enhanced through use of recombinantly produced CgtE polypeptides of the present invention. Recombinant techniques enable production of the recombinant CgtE polypeptides in the large amounts that are required for large-scale in vitro oligosaccharide, glycoprotein and glycolipid modification.

In some embodiments, suitable oligosaccharides, glycoproteins, and glycolipids for use by the CgtE polypeptides and methods of the invention can be glycoproteins and glycolipids immobilized on a solid support during the glycosylation reaction. The term "solid support" also encompasses semi-solid supports. Preferably, the target glycoprotein or glycolipid is reversibly immobilized so that the respective glycoprotein or glycolipid can be released after the glycosylation reaction is completed. Many suitable matrices are known to those of skill in the art. Ion exchange, for example, can be employed to temporarily immobilize a glycoprotein or glycolipid on an appropriate resin while the glycosylation reaction proceeds. A ligand that specifically binds to the glycoprotein or glycolipid of interest can also be used for affinity-based immobilization. For example, antibodies that specifically bind to a glycoprotein are suitable. Also, where the glycoprotein of interest is itself an antibody or contains a fragment thereof, one can use protein A or G as the affinity resin. Dyes and other molecules that specifically bind to a glycoprotein or glycolipid of interest are also suitable.

Preferably, when the acceptor saccharide is a truncated version of the full-length glycoprotein, it preferably includes the biologically active subsequence of the full-length glycoprotein. Exemplary biologically active subsequences include, but are not limited to, enzyme active sites, receptor binding sites, ligand binding sites, complementarity determining regions of antibodies, and antigenic regions of antigens.

IX. Production of Galactosylated Products

CgtE polypeptides can be used to make galactosylated products in in vitro reactions mixes or by in vivo reactions, e.g., by fermentative growth of recombinant microorganisms that comprise nucleotides that encode CgtE polypeptides.

A. In Vitro Reactions

The CgtE polypeptides can be used to make galactosylated products in in vitro reactions mixes. The in vitro reaction mixtures can include permeabilized microorganisms comprising the CgtE polypeptides, partially purified CgtE polypeptides, or purified CgtE polypeptides; as well as donor substrates acceptor substrates, and appropriate reaction buffers. For in vitro reactions, the recombinant glycosyltransferase proteins, such as CgtE polypeptides, acceptor substrates, donor substrates and other reaction mixture ingredients are combined by admixture in an aqueous reaction medium. Additional glycosyltransferases can be used in combination with the CgtE polypeptides, depending on the desired galactosylated product. The medium generally has a pH value of about 5 to about 8.5. The selection of a medium is based on the ability of the medium to maintain pH value at the desired level. Thus, in some embodiments, the medium is buffered to a pH value of about 7.5. If a buffer is not used, the pH of the medium should be maintained at about 5 to 8.5, depending upon the particular glycosyltransferase used. For CgtE polypeptides, the pH range is preferably maintained from about 6.0 to 8.0. For sialyltransferases, the range is preferably from about 5.5 to about 8.0.

Enzyme amounts or concentrations are expressed in activity units, which is a measure of the initial rate of catalysis. One activity unit catalyzes the formation of 1 μmol of product per minute at a given temperature (typically 37° C.) and pH value (typically 7.5). Thus, 10 units of an enzyme is a catalytic amount of that enzyme where 10 μmol of substrate are converted to 10 μmol of product in one minute at a temperature of 37° C. and a pH value of 7.5.

The reaction mixture may include divalent metal cations ($Mg^{2+}$, $Mn^{2+}$). The reaction medium may also comprise solubilizing detergents (e.g., Triton or SDS) and organic solvents such as methanol or ethanol, if necessary. The enzymes can be utilized free in solution or can be bound to a support such as a polymer. The reaction mixture is thus substantially homogeneous at the beginning, although some precipitate can form during the reaction.

The temperature at which an above process is carried out can range from just above freezing to the temperature at which the most sensitive enzyme denatures. That temperature range is preferably about 0° C. to about 45° C., and more preferably at about 20° C. to about 37° C.

The reaction mixture so formed is maintained for a period of time sufficient to obtain the desired high yield of desired oligosaccharide determinants present on oligosaccharide groups attached to the glycoprotein to be glycosylated. For large-scale preparations, the reaction will often be allowed to proceed for between about 0.5-240 hours, and more typically between about 1-36 hours.

One or more of the glycosyltransferase reactions can be carried out as part of a glycosyltransferase cycle. Preferred conditions and descriptions of glycosyltransferase cycles have been described. A number of glycosyltransferase cycles (for example, sialyltransferase cycles, galactosyltransferase cycles, and fucosyltransferase cycles) are described in U.S. Pat. No. 5,374,541 and WO 9425615 A. Other glycosyltransferase cycles are described in Ichikawa et al. *J. Am. Chem. Soc.* 114:9283 (1992), Wong et al. *J. Org. Chem.* 57: 4343 (1992), DeLuca, et al., *J. Am. Chem. Soc.* 117:5869-5870 (1995), and Ichikawa et al. In *Carbohydrates and Carbohydrate Polymers*. Yaltami, ed. (ATL Press, 1993).

Other glycosyltransferases can be substituted into similar transferase cycles as have been described in detail for the fucosyltransferases and sialyltransferases. In particular, the glycosyltransferase can also be, for instance, glucosyltransferases, e.g., Alg8 (Stagljov et al., *Proc. Natl. Acad. Sci. USA* 91:5977 (1994)) or Alg5 (Heesen et al. *Eur. J. Biochem.* 224:71 (1994)), N-acetylgalactosaminyltransferases such as, for example, $\alpha(1,3)$ N-acetylgalactosaminyltransferase, $\beta(1,4)$ N-acetylgalactosaminyltransferases (Nagata et al. *J. Biol. Chem.* 267:12082-12089 (1992) and Smith et al. *J. Biol. Chem.* 269:15162 (1994)) and polypeptide N-acetylgalactosaminyltransferase (Homa et al. *J. Biol. Chem.* 268:12609 (1993)). Suitable N-acetylglucosaminyltransferases include GnTI (2.4.1.101, Hull et al., *BBRC* 176:608 (1991)), GnTII, and GnTIII (Ihara et al. *J. Biochem.* 113:692 (1993)), GnTV (Shoreiban et al. *J. Biol. Chem.* 268: 15381 (1993)), O-linked N-acetylglucosaminyltransferase (Bierhuizen et al. *Proc. Natl. Acad. Sci. USA* 89:9326 (1992)), N-acetylglucosamine-1-phosphate transferase (Rajput et al. *Biochem J.* 285:985 (1992), and hyaluronan synthase. Suitable mannosyltransferases include $\alpha(1,2)$ mannosyltransferase, $\alpha(1,3)$ mannosyltransferase, $\beta(1,4)$ mannosyltransferase, Dol-P-Man synthase, OCh1, and Pmt1.

For the above glycosyltransferase cycles, the concentrations or amounts of the various reactants used in the processes depend upon numerous factors including reaction conditions such as temperature and pH value, and the choice and amount of acceptor saccharides to be glycosylated. Because the glycosylation process permits regeneration of activating nucleotides, activated donor sugars and scavenging of produced PPi in the presence of catalytic amounts of the enzymes, the process is limited by the concentrations or amounts of the stoichiometric substrates discussed before. The upper limit for the concentrations of reactants that can be used in accordance with the method of the present invention is determined by the solubility of such reactants.

Preferably, the concentrations of activating nucleotides, phosphate donor, the donor sugar and enzymes are selected such that glycosylation proceeds until the acceptor is consumed. The considerations discussed below, while in the context of a sialyltransferase, are generally applicable to other glycosyltransferase cycles.

Each of the enzymes is present in a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

B. In vivo Reactions

The CgtE polypeptides can be used to make galactosylated products by in vivo reactions, e.g., fermentative growth of recombinant microorganisms comprising the CgtE polypeptides. Fermentative growth of recombinant microorganisms can occur in the presence of medium that includes an acceptor substrate and a donor substrate or a precursor to a donor substrate, e.g., galactose or GalNAc. See, e.g., Priem et al., *Glycobiology* 12:235-240 (2002). The microorganism takes up the acceptor substrate and the donor substrate or the precursor to a donor substrate and the addition of the donor substrate to the acceptor substrate takes place in the living cell. The microorganism can be altered to facilitate uptake of the acceptor substrate, e.g., by expressing a sugar transport protein. For example, where lactose is the acceptor saccharide, *E. coli* cells that express the LacY permease can be used. Other methods can be used to decrease breakdown of an acceptor saccharide or to increase production of a donor saccharide or a precursor of the donor saccharide. In some embodiments, production of galactosylated products is enhanced by manipulation of the host microorganism. For example, in *E. coli*, break down of sialic acid can be minimized by using a host strain that is lack CMP-sialate synthase (NanA-). (In *E. coli*, CMP-sialate synthase appears to be a catabolic enzyme.) Also in *E. coli*, when lactose is, for example, the acceptor saccharide or an intermediate in synthesizing the galactosylated product, lactose breakdown can be minimized by using host cells that are LacZ-.

C. Characterization of and Isolation of Galactosylated Products

The production of galactosylated products can be monitored by e.g., determining that production of the desired product has occurred or by determining that a substrate such as the acceptor substrate has been depleted. Those of skill will recognize that galactosylated products such as oligosaccharide, can be identified using techniques such as chromatography, e.g., using paper or TLC plates, or by mass spectrometry, e.g., MALDI-TOF spectrometry, or by NMR spectroscopy. Methods of identification of galactosylated products are known to those of skill in the art and are found, e.g., in U.S. Pat. No. 6,699,705, which is herein incorporated by reference for all purposes and in Varki et al., *Preparation and Analysis of Glycoconjugates*, in Current Protocols in Molecular Biology, Chapter 17 (Ausubel et al. eds, 1993).

In some embodiments, the CgtE polypeptides and methods of the present invention are used to enzymatically synthesize a glycoprotein or glycolipid that has a substantially uniform glycosylation pattern. The glycoproteins and glycolipids include a saccharide or oligosaccharide that is attached to a protein, glycoprotein, lipid, or glycolipid for which a glycoform alteration is desired. The saccharide or oligosaccharide includes a structure that can function as an acceptor substrate for a glycosyltransferase. When the acceptor substrate is glycosylated, the desired oligosaccharide moiety is formed. The desired oligosaccharide moiety is one that imparts the desired biological activity upon the glycoprotein or glycolipid to which it is attached. In the compositions of the invention, the preselected saccharide residue is linked to at least about 30% of the potential acceptor sites of interest. More preferably, the preselected saccharide residue is linked to at least about 50% of the potential acceptor substrates of interest, and still more preferably to at least 70% of the potential acceptor substrates of interest. In situations in which the starting glycoprotein or glycolipid exhibits heterogeneity in the oligosaccharide moiety of interest (e.g., some of the oligosaccharides on the starting glycoprotein or glycolipid already have the preselected saccharide residue attached to the acceptor substrate of interest), the recited percentages include such pre-attached saccharide residues.

The term "altered" refers to the glycoprotein or glycolipid of interest having a glycosylation pattern that, after application of the CgtE polypeptides and methods of the invention, is different from that observed on the glycoprotein as originally produced. An example of such glycoconjugates are glycoproteins in which the glycoforms of the glycoproteins are different from those found on the glycoprotein when it is produced by cells of the organism to which the glycoprotein is native. Also provided are CgtE polypeptides and methods of using such proteins for enzymatically synthesizing glycoproteins and glycolipids in which the glycosylation pattern of these glycoconjugates are modified compared to the glycosylation pattern of the glycoconjugates as originally produced by a host cell, which can be of the same or a different species than the cells from which the native glycoconjugates are produced.

One can assess differences in glycosylation patterns not only by structural analysis of the glycoproteins and glycolipids, but also by comparison of one or more biological activities of the glycoconjugates. For example, a glycoprotein having an "altered glycoform" includes one that exhibits an improvement in one more biological activities of the glycoprotein after the glycosylation reaction compared to the unmodified glycoprotein. For example, an altered glycoconjugate includes one that, after application of the CgtE polypeptides and methods of the invention, exhibits a greater binding affinity for a ligand or receptor of interest, a greater therapeutic half-life, reduced antigenicity, and targeting to specific tissues. The amount of improvement observed is preferably statistically significant, and is more preferably at least about a 25% improvement, and still more preferably is at least about 30%, 40%, 50%, 60%, 70%, and even still more preferably is at least 80%, 90%, or 95%.

The products produced using CgtE polypeptides can be used without purification. However, standard, well known techniques, for example, thin or thick layer chromatography, ion exchange chromatography, or membrane filtration can be used for recovery of glycosylated saccharides. Also, for example, membrane filtration, utilizing a nanofiltration or reverse osmotic membrane as described in commonly assigned AU Patent No. 735695 may be used. As a further example, membrane filtration wherein the membranes have a molecular weight cutoff of about 1000 to about 10,000 Daltons can be used to remove proteins. As another example, nanofiltration or reverse osmosis can then be used to remove salts. Nanofilter membranes are a class of reverse osmosis membranes which pass monovalent salts but retain polyvalent salts and uncharged solutes larger than about 200 to about 1000 Daltons, depending upon the membrane used. Thus, for example, the oligosaccharides produced by the compositions and methods of the present invention can be retained in the membrane and contaminating salts will pass through.

X. Multienzyme Oligosaccharide Synthesis

As discussed above, in some embodiments, two or more enzymes may be used to form a desired oligosaccharide, including an oligosaccharide determinant on a glycoprotein or glycolipid. For example, a particular oligosaccharide determinant might require addition of a galactose, a sialic acid, and a fucose in order to exhibit a desired activity. Accordingly, the invention provides methods in which two or more glycosyltransferases, e.g., a CgtE polypeptide, and another glycosyltransferase, such as a fucosyltransferase or a sialyltransferase, are used to obtain high-yield synthesis of a desired oligosaccharide determinant.

The CgtE polypeptides, prepared as described herein, can be used in combination with a multitude of glycosyltransferases. For example, one can use a combination of recombinant CgtE polypeptides and a recombinant fucosyltransferases, e.g., an *H. pylori* α-1,3/4-fucosyltransferase. For example fucosyltransferases from *Helicobacter pylori* are disclosed in U.S. Pat. Nos. 6,534,298 and 6,238,894; WO2004009838, published Jan. 29, 2004; U.S. Ser. No. 10/764,212, filed Jan. 22, 2004; each of which are herein incorporated by reference for all purposes. Bacterial glycosyltransferases can also be used, including α2,3-sialyltransferases, bifunctional α2,3-2,8-sialyltransferases, β-1,4-GalNActransferases and β-1,3-Galactosyltransferases which have been isolated from *Campylobacter jejuni* and are disclosed in U.S. Pat. No. 6,699,705, issued Mar. 2, 2004, herein incorporated by reference for all purposes. Additional sialyltransferases are disclosed in U.S. Pat. No. 6,096,529, issued Aug. 1, 2000 and in U.S. Ser. No. 60/610,807, filed Sep. 17, 2004; both of which are herein incorporated by reference for all purposes. Similarly, the recombinant glycosyltransferases can be used with recombinant accessory enzymes, which may or may not be fused to the glycosyltransferase thereby forming a fusion protein. In other embodiments, the CgtE polypeptides and additional glycosyltransferases and/or accessory enzymes are produced in the same cell and used to synthesize a desired end product.

In some cases, a glycoprotein- or glycolipid linked oligosaccharide will include an acceptor substrate for the particular glycosyltransferase of interest upon in vivo biosynthesis of the glycoprotein or glycolipid. Such glycoproteins or glycolipids can be glycosylated using the recombinant glycosyltransferase fusion proteins and methods of the invention without prior modification of the glycosylation pattern of the glycoprotein or glycolipid, respectively. In other cases, however, a glycoprotein or glycolipid of interest will lack a suitable acceptor substrate. In such cases, the methods of the invention can be used to alter the glycosylation pattern of the glycoprotein or glycolipid so that the glycoprotein- or glycolipid-linked oligosaccharides then include an acceptor substrate for the glycosyltransferase-catalyzed attachment of a preselected saccharide unit of interest to form a desired oligosaccharide moiety.

Glycoprotein- or glycolipid linked oligosaccharides optionally can be first "trimmed," either in whole or in part, to expose either an acceptor substrate for the glycosyltransferase or a moiety to which one or more appropriate residues can be added to obtain a suitable acceptor substrate. Enzymes such as glycosyltransferases and endoglycosidases are useful for the attaching and trimming reactions. For example, a glycoprotein that displays "high mannose"-type oligosaccharides can be subjected to trimming by a mannosidase to obtain an acceptor substrate that, upon attachment of one or more preselected saccharide units, forms the desired oligosaccharide determinant.

The methods are also useful for synthesizing a desired oligosaccharide moiety on a protein or lipid that is unglycosylated in its native form. A suitable acceptor substrate for the corresponding glycosyltransferase can be attached to such proteins or lipids prior to glycosylation using the methods of the present invention. See, e.g., U.S. Pat. No. 5,272,066 for methods of obtaining polypeptides having suitable acceptors for glycosylation.

Thus, in some embodiments, the invention provides methods for in vitro sialylation of saccharide groups present on a glycoconjugate that first involves modifying the glycoconjugate to create a suitable acceptor.

It must be noted that as used herein and in the appended claims, the singular forms "a", "and", and "the" include plural referents unless the context clearly dictates otherwise. Thus, for example, reference to "a nucleic acid" includes a plurality of such nucleic acids and reference to "the polypeptide" includes reference to one or more polypeptides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. Citations are incorporated herein by reference.

EXAMPLES

Example 1

Cloning and Expression of CgtE from *C. jejuni* LIO87

Open reading frames from the *C. jejuni* LIO87 LOS locus were expressed in *E. coli*. Cells were harvested and cell extracts were made and assayed for glycosyltransferase activity using UDP-Glc, UDP-GlcNAc, UDP-Gal and UDP-GalNAc as donor substrates and fluorescent derivatives of Glc, Gal, Lac, LacNAc and Gal-α-1,4-Lac as acceptor substrates. ORF #7 had activity with either UDP-Gal and UDP-GalNAc as donor substrate and the Gal-α-1,4-Lac (Pk) derivative as acceptor substrate. ORF #7 was designated CgtE (Campylobacter glycosyltransferase; E is an internal coding) and was further characterized.

The nucleic acid encoding CgtE from *C. jejuni* LIO87 was cloned into an expression vector, pCWori+, either alone (construct CJL-107) or as a C-terminal fusion with the *E. coli* maltose-binding (MalE) protein (construct CJL-101). CJL-101 and CJL-107 were electroporated into *E. coli* strain AD202. CgtE protein was expressed with the MalE tag (10 to 15 units per liter) and expressed as an untagged protein (30 to 40 units per liter).

Example 2

Characterization of CgtE Activity from *C. jejuni* LIO87

CgtE enzymatic activity was characterized further. CgtE activity was optimal from pH 7 to 7.5. Divalent cations were necessary for activity with $MnCl_2$ providing the optimal activity (two-fold higher than the activity observed with $MgCl_2$).

CgtE was observed to transfer both Gal and GalNAc residues to a terminal α-Gal residue. The ability of CgtE to transfer a sugar to a terminal α-GalNAc residue was also assayed and results are shown in Table 1. CgtE used both Galα-Lac-FCHASE and GalNAc-α-FCHASE as acceptor substrate. CgtE enzymatic activity was higher when Galα-Lac-FCHASE was used as the acceptor substrate.

TABLE 1

Substrate specificity of CgtE (CJL-107).

| Acceptor | Donor | Activity (mU/mL) |
|---|---|---|
| Galα-Lac-FCHASE | UDP-GalNAc | 63.5 |
| Galα-Lac-FCHASE | UDP-Gal | 7.0 |
| GalNAc-α-FCHASE | UDP-GalNAc | 0.3 |
| GalNAC-α-FCHASE | UDP-Gal | 0.6 |

Figure 2:
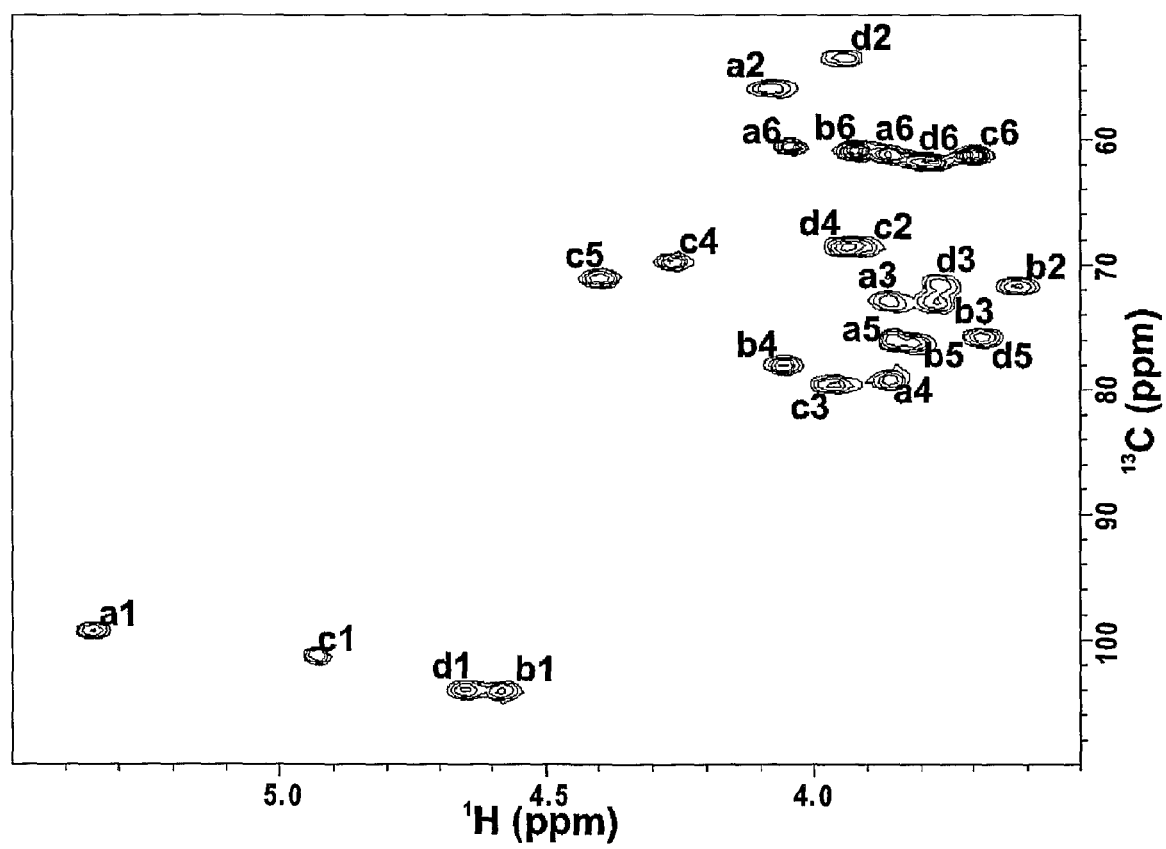
FIG. 2 provides the $^1$H—$^{13}$C HSQC spectrum of the tetrasaccharide p-nitrophenyl compound. Cross-peaks are labeled as follows: a for βGlcNAc, b for βGal(1-4), c for αGal(1-4) and d for β3GalNAc(1-3). The carbon resonances at positions a4, b4 and c3 exhibit downfield shifts in comparison with monosaccharide values, consistent with their participation in a glycosidic bond.

In order to determine the regio- and stereo-specificity of CgtE activity, a 15,000 rpm supernatant of CJL-107 was used to transfer a GalNAc residue to Galα-1,4-Galβ-1,4-GlcNAc-p-nitrophenyl. See, e.g., FIG. 1. In the assay, 6.9 mg of GalNAcβ-1,3-Galα-1,4-Galβ-1,4-GlcNAc-p-nitrophenyl was synthesized. The $^1H$ NMR resonances were assigned to the tetrasaccharide compound through the use of 2D homonuclear COSY and TOCSY spectra See, e.g., Table 2. These assignments were then used to identify cross-peaks in a $^1H$—$^{13}C$ HSQC spectrum which correlates the chemical shift of a proton atom with its directly bonded carbon neighbor. See, e.g., FIG. 2. Because inter-residue connectivities can be established across glycosidic bonds using a $^1H$—$^{13}C$ HMBC pulse sequence, an HMBC spectra of the tetrasaccharide compound was obtained to establish the covalent linkages between sugar residues. The HMBC spectra confirmed that the CgtE protein transferred a GalNAc residue to α-Gal on the trisaccharide precursor through a β1→3 linkage. Consistent with the HMBC spectra, the carbon atom at position C3 of αGal was shifted downfield in comparison with monosaccharide values, which is a qualitative indicator that it is involved in a glycosidic linkage with the adjacent βGalNAc residue. See, e.g., FIG. 2.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

Informal Sequence Listing

CgtE nucleic acid

SEQ ID NO: 1

ATGCCTAAAATTTCAATCATCTTGC-
CAACTTTTAATGTACAAAAATATATAG

CCAAAGCTTTAGAAAGTTGTATCAAT-
CAAAGTTTTAAAGATATAGAAATAAT

TGTAGTGGATGATTGTGGAAGT-
GATAAAAGTATAGATATAGCTAAAGAATAT

GCCAAAAAAGATGAAA-
GAATAAAAATAATTCACAATGAAGAAAATTTAGGTC

TTTTAAGAGCTAGATATGAAGGAGT-
TAAGGCAGCTGGGGGGGGGTATATTAT

GTTTTTAGACCCTGATGATTATTTA-
GAACTTAATGCTTGTGAAGAGTGTCTG

AGAATTTTAAACACTGAAAAAGAAAGT-
GATTTTATATGGTTTGATTTTATAT

ATAAAAGAATTTCAGGGGTTATAAAT-
AGGGGAAATTTTTTACAAGATCAAAC

TTTTACTATTTTTGAATATTGT-
GAGAATATCATAATTCAAAATAAAAATATC

TGTTATTGGAATCTTTGTTCTAAACT-
TATTAAAACAGAAATATATTTAGCAT

CTTTTTCTTTTTAGAAAAAGAGATAT-
TAAATACTAGATTAATTATGGCAGA

AGATGCATTAATTTATTTTTTTAT-
TATTTTAAATTGTGGAAAAATTACTACT

AGTGCAAAAAATATTTATTATTATTGT-
GAAAATGACAATAGTTCTGTTGGGA

CTAATGATATTGTCAAAAT-
TGAAAAAAACTTACAAGATGAAAAAATGGTTAT

TGGAATTTTACTAGAATTTTTAAATCAT-
CATAAAAAGAATATTGAATTGTAT

TTGTATGTTTTTTTAAAAATAATGATTG-
GTAAATTAATCGTATATAAATTAC

ATCGAGAAATAAAACTATATCGAT-
TAAAATATAATTATATGATATATACAAT

GAAAAAAATAAAAAAATAAATT-
TATAATAAAATATTTTTTATTGAAAAGATTT

TTGATGGAAAAGTATTTTAAAAATAAATTTAATTGA

CgtE amino acid

SEQ ID NO: 2

MPKISIILPTFNVEKYIAKALESCINQS-
FKDIEIIVVDDCGSDKSIDIAKEY

AKKDERIKIIHNEENLGLLRARYEGV-
KAAGGGYIMFLDPDDYLELNACEECV

RILNTEKESDFIWFDFIYKRISGVIN-
RGNFLQDQTFTIFEYCENIIIQNKNI

CYWNLCSKLIKTEIYLASFSFLEKEILN-
TRLIMAEDALIYFFIILNCGKITT

SAKNIYYYCENDNSSVGTNDIVKIEKN-
LQDEKMVIGILLEFLNHHKKNIELY

LYVFLKIMIGKLIVYKLHREIKLYR-
LKYNYMIYTMKKIKNKFIIKYFLLKRF

LMEKYFKNKFN

---

What is claimed is:

1. A composition comprising an isolated or recombinant β-1,3-N-acetylgalactosaminyltransferase polypeptide, a donor substrate comprising the galactose moiety GalNAc, and an acceptor substrate comprising a terminal galactose residue wherein the β-1,3-N-acetylgalactosaminyltransferase polypeptide comprises an amino acid sequence with at least 95% identity to the full length of SEQ ID NO:2, and wherein the β-1,3-N-acetylgalactosaminyltransferase polypeptide transfers the galactose moiety from a donor substrate to an acceptor substrate.

2. The composition of claim 1, wherein the β-1,3-N-acetylgalactosaminyltransferase polypeptide comprises an amino acid sequence with at least 97% identity to the full length of SEQ ID NO:2.

3. The composition of claim 1, wherein the β-1,3-N-acetylgalactosaminyltransferase polypeptide comprises an amino acid sequence with at least 99% identity to the full length of SEQ ID NO:2.

4. The composition of claim 1, wherein the β-1,3-N-acetylgalactosaminyltransferase polypeptide comprises the amino acid sequence of SEQ ID NO:2.

5. The composition of claim 1, wherein the β-1,3-N-acetylgalactosaminyltransferase polypeptide comprises amino acid residues 5-167 of SEQ ID NO:2.

6. The composition of claim 2, wherein the β-1,3-N-acetylgalactosaminyltransferase polypeptide comprises amino acid residues 5-167 of SEQ ID NO:2.

7. The composition of claim 3, wherein the β-1,3-N-acetylgalactosaminyltransferase polypeptide comprises amino acid residues 5-167 of SEQ ID NO:2.

8. The composition of claim 1, wherein the β-1,3-N-acetylgalactosaminyltransferase polypeptide comprises in corresponding positions, the amino acid residues identical to the amino acid residues at positions 5, 7, 9,10, 12, 14-16, 21-23, 27, 33-39, 43, 48, 49, 51-54, 56, 58, 59, 62, 65-69, 73, 74, 77, 79, 81, 85, 86, 88-90, 92, 93, 101, 104, 107, 110, 111, 116, 132, 135, and 154 of SEQ ID NO:2 and;

further optionally comprises conservative amino acid substitutions corresponding to positions 6, 11, 17, 19, 25, 28, 28, 29, 31, 42, 45-47, 50, 60, 61, 78, 87, 95, 98, 102, 106, 136, 138, 142, 151, 156, 163, and 167 of SEQ ID NO:2 such that the conserved residues are interchangeable within the following groups:
   (i) Alanine (A), Glycine (G);
   (ii) Aspartic acid (D), Glutamic acid (E);
   (iii) Asparagine (N), Glutamine (Q);
   (iv) Arginine (R), Lysine (K);
   (v) Isoleucine (I), Leucine (L), Methionine (M), Valine (V), Alanine (A);
   (vi) Phenylalanine (F), Tyrosine (Y), Tryptophan (W);
   (vii) Serine (S), Threonine (T), Cysteine (C); and
   (viii) Cysteine (C), Methionine (M).

9. The composition of claim 2, wherein the β-1,3-N-acetylgalactosaminyltransferase polypeptide comprises in corresponding positions, the amino acid residues identical to the amino acid residues at positions 5, 7, 9,10, 12, 14-16, 21-23, 27, 33-39, 43, 48, 49, 51-54, 56, 58, 59, 62, 65-69, 73, 74, 77, 79, 81, 85, 86, 88-90, 92, 93, 101, 104, 107, 110, 111, 116, 132, 135, and 154 of SEQ ID NO:2 and;

further optionally comprises conservative amino acid substitutions corresponding to positions 6, 11, 17, 19, 25, 28, 28, 29, 31, 42, 45, 46, 47, 50, 60, 61, 78, 87, 95, 98, 102, 106, 136, 138, 142, 151, 156, 163, and 167 of SEQ ID NO:2 such that the conserved residues are interchangeable within the following groups:
   (i) Alanine (A), Glycine (G);
   (ii) Aspartic acid (D), Glutamic acid (E);
   (iii) Asparagine (N), Glutamine (Q);
   (iv) Arginine (R), Lysine (K);

(v) Isoleucine (I), Leucine (L), Methionine (M), Valine (V), Alanine (A);
(vi) Phenylalanine (F), Tyrosine (Y), Tryptophan (W);
(vii) Serine (S), Threonine (T), Cysteine (C); and
(viii) Cysteine (C), Methionine (M).

10. The composition of claim 3, wherein the β-1,3-N-acetylgalactosaminyltransferase polypeptide comprises in corresponding positions, the amino acid residues identical to the amino acid residues at positions 5, 7, 9, 10, 12, 14-16, 21-23, 27, 33-39, 43, 48, 49, 51-54, 56, 58, 59, 62, 65-69, 73, 74, 77, 79, 81, 85, 86, 88-90, 92, 93, 101, 104, 107, 110, 111, 116, 132, 135, and 154 of SEQ ID NO:2 and;

further optionally comprises conservative amino acid substitutions corresponding to positions 6, 11, 17, 19, 25, 28, 28, 29, 31, 42, 45, 46, 47, 50, 60, 61, 78, 87, 95, 98, 102, 106, 136, 138, 142, 151, 156, 163, and 167 of SEQ ID NO:2 such that the conserved residues are interchangeable within the following groups:
(i) Alanine (A), Glycine (G);
(ii) Aspartic acid (D), Glutamic acid (E);
(iii) Asparagine (N), Glutamine (Q);
(iv) Arginine (R), Lysine (K);
(v) Isoleucine (I), Leucine (L), Methionine (M), Valine (V), Alanine (A);
(vi) Phenylalanine (F), Tyrosine (Y), Tryptophan (W);
(vii) Serine (S), Threonine (T), Cysteine (C); and
(viii) Cysteine (C), Methionine (M).

11. A method of producing a galactosylated product saccharide, the method comprising the step of:
 a. contacting an acceptor substrate comprising a terminal galactose residue with a donor substrate comprising a GalNAc galactose moiety and an isolated or recombinant β-1,3-N-acetylgalactosaminyltransferase polypeptide with at least 95% identity to SEQ ID NO:2; and
 b. allowing transfer of a galactose moiety to the acceptor saccharide to occur, thereby producing the galactosylated product saccharide.

12. The method of claim 11, wherein the β-1,3-N-acetylgalactosaminyltransferase polypeptide comprises an amino acid sequence with at least 97% identity to SEQ ID NO:2.

13. The method of claim 11, wherein the β-1,3-N-acetylgalactosaminyltransferase polypeptide comprises an amino acid sequence with at least 99% identity to SEQ ID NO:2.

14. The method of claim 11, wherein the β-1,3-N-acetylgalactosaminyltransferase polypeptide comprises an amino acid sequence of SEQ ID NO:2.

15. The method of claim 11, wherein the method is performed to achieve production of greater than 50 grams of said galactosylated product saccharide in a single reaction.

* * * * *

SEQUENCE LISTING

<160> NUMBER OF SEQ ID NOS: 12

<210> SEQ ID NO 1
<211> LENGTH: 972
<212> TYPE: DNA
<213> ORGANISM: Campylobacter jejuni
<220> FEATURE:
<223> OTHER INFORMATION: Campylobacter jejuni LIO87 type strain
      lipooligosaccharide (LOS) locus open reading frame #7 (ORF #7)
      designated CtgE (Campylobacter glycosyltransferase; E is an
      internal coding) nucleic acid

<400> SEQUENCE: 1
atgcctaaaa tttcaatcat cttgccaact tttaatgtag aaaatatat agccaaagct      60 ttagaaagtt gtatcaatca aagttttaaa gatatagaaa taattgtagt ggatgattgt     120
ggaagtgata aaagtataga tatagctaaa gaatatgcca aaaagatga agaataaaa      180 ataattcaca atgaagaaaa tttaggtctt taagagcta gatatgaagg agttaaggca     240 gctgggggggg ggtatattat gtttttagac cctgatgatt atttagaact taatgcttgt   300
gaagagtgtg tgagaatttt aaacactgaa aaagaaagtg attttatatg gtttgatttt   360
atatataaaa gaatttcagg ggttataaat aggggaaatt ttttacaaga tcaaactttt   420 actattttttg aatattgtga gaatatcata attcaaaata aaaatatctg ttattggaat  480
ctttgttcta aacttattaa aacagaaata tatttagcat ctttttcttt tttagaaaaa   540
gagatattaa atactagatt aattatggca gaagatgcat taatttattt ttttattatt   600
ttaaattgtg gaaaaattac tactagtgca aaaatatttt attattattg tgaaaatgac   660
aatagttctg ttgggactaa tgatattgtc aaaattgaaa aaaacttaca agatgaaaaa   720
atggttattg aattttact agaattttta aatcatcata aaagaatat tgaattgtat    780 ttgtatgttt tttaaaaaat aatgattggt aaattaatcg tatataaatt acatcgagaa  840
ataaaactat atcgattaaa atataattat atgatatata caatgaaaaa aataaaaaat  900
aaatttataa taaatatttt tttattgaaa agattttga tggaaaagta ttttaaaaat   960
aaatttaatt ga                                                      972

-continued

<210> SEQ ID NO 2
<211> LENGTH: 323
<212> TYPE: PRT
<213> ORGANISM: Campylobacter jejuni
<220> FEATURE:
<223> OTHER INFORMATION: Campylobacter jejuni LIO87 type strain
      lipooligosaccharide (LOS) locus open reading frame #7 (ORF #7)
      designated CtgE (Campylobacter glycosyltransferase; E is an
      internal coding) beta-1,3-N-acetylgalactosaminyltransferase

<400> SEQUENCE: 2

Met Pro Lys Ile Ser Ile Ile Leu Pro Thr Phe Asn Val Glu Lys Tyr
 1               5                  10                  15

Ile Ala Lys Ala Leu Glu Ser Cys Ile Asn Gln Ser Phe Lys Asp Ile
            20                  25                  30

Glu Ile Ile Val Val Asp Asp Cys Gly Ser Lys Ser Ile Asp Ile
        35                  40                  45

Ala Lys Glu Tyr Ala Lys Lys Asp Glu Arg Ile Lys Ile Ile His Asn
    50                  55                  60

Glu Glu Asn Leu Gly Leu Leu Arg Ala Arg Tyr Glu Gly Val Lys Ala
65                  70                  75                  80

Ala Gly Gly Gly Tyr Ile Met Phe Leu Asp Pro Asp Asp Tyr Leu Glu
                85                  90                  95

Leu Asn Ala Cys Glu Glu Cys Val Arg Ile Leu Asn Thr Glu Lys Glu
            100                 105                 110

Ser Asp Phe Ile Trp Phe Asp Phe Ile Tyr Lys Arg Ile Ser Gly Val
        115                 120                 125

Ile Asn Arg Gly Asn Phe Leu Gln Asp Gln Thr Phe Thr Ile Phe Glu
    130                 135                 140

Tyr Cys Glu Asn Ile Ile Ile Gln Asn Lys Asn Ile Cys Tyr Trp Asn
145                 150                 155                 160

Leu Cys Ser Lys Leu Ile Lys Thr Glu Ile Tyr Leu Ala Ser Phe Ser
                165                 170                 175

Phe Leu Glu Lys Glu Ile Leu Asn Thr Arg Leu Ile Met Ala Glu Asp
            180                 185                 190

Ala Leu Ile Tyr Phe Phe Ile Ile Leu Asn Cys Gly Lys Ile Thr Thr
        195                 200                 205

Ser Ala Lys Asn Ile Tyr Tyr Tyr Cys Glu Asn Asp Asn Ser Ser Val
    210                 215                 220

Gly Thr Asn Asp Ile Val Lys Ile Glu Lys Asn Leu Gln Asp Glu Lys
225                 230                 235                 240

Met Val Ile Gly Ile Leu Leu Glu Phe Leu Asn His His Lys Lys Asn
                245                 250                 255

Ile Glu Leu Tyr Leu Tyr Val Phe Leu Lys Ile Met Ile Gly Lys Leu
            260                 265                 270

Ile Val Tyr Lys Leu His Arg Glu Ile Lys Leu Tyr Arg Leu Lys Tyr
        275                 280                 285

Asn Tyr Met Ile Tyr Thr Met Lys Lys Ile Lys Asn Lys Phe Ile Ile
    290                 295                 300

Lys Tyr Phe Leu Leu Lys Arg Phe Leu Met Glu Lys Tyr Phe Lys Asn
305                 310                 315                 320

Lys Phe Asn

<210> SEQ ID NO 3
<211> LENGTH: 163
<212> TYPE: PRT
<213> ORGANISM: Artificial Sequence

```
<220> FEATURE:
<223> OTHER INFORMATION: Description of Artificial Sequence:CtgE protein
      residues 5-167, glycosyl_transf_2-related domain

<400> SEQUENCE: 3

Ser Ile Ile Leu Pro Thr Phe Asn Val Glu Lys Tyr Ile Ala Lys Ala
1               5                   10                  15

Leu Glu Ser Cys Ile Asn Gln Ser Phe Lys Asp Ile Glu Ile Ile Val
            20                  25                  30

Val Asp Asp Cys Gly Ser Asp Lys Ser Ile Asp Ile Ala Lys Glu Tyr
        35                  40                  45

Ala Lys Lys Asp Glu Arg Ile Lys Ile Ile His Asn Glu Glu Asn Leu
    50                  55                  60

Gly Leu Leu Arg Ala Arg Tyr Glu Gly Val Lys Ala Ala Gly Gly Gly
65                  70                  75                  80

Tyr Ile Met Phe Leu Asp Pro Asp Asp Tyr Leu Glu Leu Asn Ala Cys
                85                  90                  95

Glu Glu Cys Val Arg Ile Leu Asn Thr Glu Lys Glu Ser Asp Phe Ile
            100                 105                 110

Trp Phe Asp Phe Ile Tyr Lys Arg Ile Ser Gly Val Ile Asn Arg Gly
        115                 120                 125

Asn Phe Leu Gln Asp Gln Thr Phe Thr Ile Phe Glu Tyr Cys Glu Asn
    130                 135                 140

Ile Ile Ile Gln Asn Lys Asn Ile Cys Tyr Trp Asn Leu Cys Ser Lys
145                 150                 155                 160

Leu Ile Lys

<210> SEQ ID NO 4
<211> LENGTH: 161
<212> TYPE: PRT
<213> ORGANISM: Artificial Sequence
<220> FEATURE:
<223> OTHER INFORMATION: Description of Artificial Sequence:
      glycosyl_transf_2 consensus sequence residues 1-161

<400> SEQUENCE: 4

Ser Val Ile Ile Pro Thr Tyr Asn Glu Glu Lys Tyr Leu Glu Glu Thr
1               5                   10                  15

Leu Glu Ser Leu Leu Ala Gln Thr Tyr Pro Asn Phe Glu Ile Ile Val
            20                  25                  30

Val Asp Asp Gly Ser Thr Asp Gly Thr Val Glu Ile Ala Glu Glu Tyr
        35                  40                  45

Ala Lys Asn Asp Pro Arg Ile Arg Val Ile Arg Leu Glu Glu Asn Leu
    50                  55                  60

Gly Lys Ala Ala Ala Arg Asn Ala Gly Leu Lys His Ala Thr Gly Asp
65                  70                  75                  80

Tyr Ile Leu Phe Leu Asp Ala Asp Asp Glu Val Ala Pro Asp Trp Leu
                85                  90                  95

Glu Lys Leu Val Glu Leu Leu Glu Lys Asn Gly Ala Asp Ile Val Ile
            100                 105                 110

Gly Ser Arg Val Ala Ile Phe Gly Glu Thr Arg Leu Asp Gly Arg Ala
        115                 120                 125

Leu Arg Met Glu Leu Leu Leu Leu Gly Lys Leu Gly Ala Arg Ser
    130                 135                 140

Leu Gly Leu Lys Val Leu Phe Leu Ile Gly Ser Asn Ala Leu Tyr Arg
145                 150                 155                 160

Arg
```

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence:"FLAG tag"
      epitope tag for anti-FLAG antibody

<400> SEQUENCE: 5

Asp Tyr Lys Asp Asp Asp Asp Lys
 1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence:
      hexahistidine peptide epitope tag, metal chelate affinity
      ligand, affinity tag

<400> SEQUENCE: 6

His His His His His His
 1               5

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence:5-prime
      primer with NdeI site, PCR primer CJ-640 used to amplify
      nucleic acid that encodes CgtE protein

<400> SEQUENCE: 7
tttaagaaaa catatgccta aaatttcaat catc                                  34

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:3-prime
      primer with SalI site, PCR primer CJ-641 used to amplify
      nucleic acid that encodes CgtE protein

<400> SEQUENCE: 8
ggtaatctag tcgacaatta taacacattc                                       30

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:CJ42 25 mer
      Primer in heptosylTase-II, PCR primer used to
      amplify LOS locus encoding CgtE protein

<400> SEQUENCE: 9
gccattaccg tatcgcctaa ccagg                                            25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:CJ43 25 mer
      Primer in heptosylTase-I, PCR primer used to -continued

```
amplify LOS locus encoding CgtE protein

<400> SEQUENCE: 10
aaagaatacg aatttgctaa agagg                                          25

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence:purification
      or epitope tag DDDDK (EC5)

<400> SEQUENCE: 11

Asp Asp Asp Asp Lys
 1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence:6 residue
      peptide purification or epitope tag derived from
      Polyoma middle T protein

<400> SEQUENCE: 12

Glu Tyr Met Pro Met Glu
 1               5
```